United States Patent
Kaneko

(10) Patent No.: US 10,607,358 B2
(45) Date of Patent: Mar. 31, 2020

(54) EAR SHAPE ANALYSIS METHOD, EAR SHAPE ANALYSIS DEVICE, AND EAR SHAPE MODEL GENERATION METHOD

(71) Applicant: Yamaha Corporation, Hamamatsu-shi, Shizuoka-Ken (JP)

(72) Inventor: Shoken Kaneko, Hamamatsu (JP)

(73) Assignee: Yamaha Corporation, Hamamatsu-shi (JP)

( * ) Notice: Subject to any disclaimer, the term of this patent is extended or adjusted under 35 U.S.C. 154(b) by 135 days.

(21) Appl. No.: 15/920,206

(22) Filed: Mar. 13, 2018

(65) Prior Publication Data

US 2018/0204341 A1 Jul. 19, 2018

Related U.S. Application Data

(63) Continuation of application No. PCT/JP2016/073829, filed on Aug. 15, 2016.

(30) Foreign Application Priority Data

Sep. 14, 2015 (JP) ................................ 2015-180993

(51) Int. Cl.
*G06T 7/60* (2017.01)
*G01B 11/24* (2006.01)
(Continued)

(52) U.S. Cl.
CPC .............. *G06T 7/60* (2013.01); *A61B 5/107* (2013.01); *A61B 5/1077* (2013.01); *A61B 5/1079* (2013.01); *G01B 11/24* (2013.01); *G06K 9/00214* (2013.01); *G06T 7/00* (2013.01); *G06T 19/20* (2013.01); *A61B 2503/12* (2013.01); *G06T 2207/30196* (2013.01); *H04S 7/303* (2013.01); *H04S 2420/01* (2013.01)

(58) Field of Classification Search
CPC ......... A61B 5/107; A61B 5/1077; G06T 7/60; G06T 7/00; G06T 19/20; G01B 11/24; G06K 9/00214
See application file for complete search history.

(56) References Cited

U.S. PATENT DOCUMENTS

2013/0169779 A1 7/2013 Pedersen
2015/0073262 A1* 3/2015 Roth .................... A61B 5/1077
600/411
2018/0249275 A1* 8/2018 Ghorbal .................. H04S 7/301

FOREIGN PATENT DOCUMENTS

JP 2007-299070 A 11/2007
JP 2013-168924 A 8/2013

OTHER PUBLICATIONS

Japanese-language Office Action issued in counterpart Japanese Application No. 2017-539786 dated Jun. 25, 2019 with English translation (12 pages).
(Continued)

*Primary Examiner* — Leon Flores
(74) *Attorney, Agent, or Firm* — Crowell & Moring LLP

(57) ABSTRACT

An ear shape analysis method implemented by a computer includes generating a first ear shape data set by applying a first principal component weight vector to an ear shape model reflecting statistical tendencies of three-dimensional shapes of ears; and identifying from the generated first ear shape data set an estimated three-dimensional shape of a target ear corresponding to a target ear image represented by image data.

15 Claims, 12 Drawing Sheets

(51) Int. Cl.
| | |
|---|---|
| *A61B 5/107* | (2006.01) |
| *G06T 7/00* | (2017.01) |
| *G06T 19/20* | (2011.01) |
| *G06K 9/00* | (2006.01) |
| *H04S 7/00* | (2006.01) |

(56) References Cited

OTHER PUBLICATIONS

International Search Report (PCT/ISA/210) issued in PCT Application No. PCT/JP2016/073829 dated Sep. 20, 2016 with English translation (five pages).
Japanese-language Written Opinion (PCT/ISA/237) issued in PCT Application No. PCT/JP2016/073829 dated Sep. 20, 2016 (four pages).
Dellepiane et al., "Reconstructing head models from photographs for individualized 3D-audio processing", Pacific Graphics, 2008, pp. 1719-1727 (10 pages total), vol. 27, No. 7, Blackwell Publishing Ltd.
Chui et al., "A new point matching algorithm for non-rigid registration", Computer Vision and Image Understanding 89, Academic Press, 2003, pp. 114-141, Elsevier Science.
Jian et al., "Robust Point Set Registration Using Gaussian Mixture Models", IEEE Transactions on Pattern Analysis and Machine Intelligence, Aug. 2011, pp. 1633-1645, IEEE Computer Society.
Katz, "Boundary element method calculation of individual head-related transfer function. I. Rigid model calculation", The Journal of the Acoustical Society of America 110, Nov. 2001, pp. 2440-2447.
Extended European Search Report issued in counterpart European Application No. 16846180.4 dated Mar. 14, 2019 with English translation (six (6) pages).

\* cited by examiner

EAR SHAPE ANALYSIS METHOD, EAR SHAPE ANALYSIS DEVICE, AND EAR SHAPE MODEL GENERATION METHOD

BACKGROUND OF THE INVENTION

Field of the Invention

The present invention relates to a technology for analyzing an ear shape that is used in calculating head-related transfer functions.

Description of the Related Art

Reproducing an audio signal representing a sound with head-related transfer functions convolved therein (binaural playback) allows a listener to perceive a sound field with a realistic feeling, in which sound field a location of a sound image can be clearly perceived. Head-related transfer functions may for instance be calculated from a sound recorded at the ear holes of either the head of a listener or a dummy head of a given shape. However, use of a dummy head for the calculation involves a problem in that the listener is unable to perceive a location of a sound image appropriately if the shape of the head of the listener and that of the dummy head do not match each other. Measuring a head-related transfer function directly from the head of the listener also involves a problem in that considerable physical and psychological burdens are imposed on the listener during measurement.

Against the background described above, Non-Patent Document 1, for example, proposes a technique in which a head-related transfer function is calculated for a listener from images of the head of the listener that have been captured from different directions. Specifically, the head shape of the listener is estimated by use of a morphing technique in which a standard head shape prepared in advance is deformed so as to resemble the head shape of the listener as captured in the images, and a head-related transfer function is calculated for the listener from the results of this estimation.

RELATED ART DOCUMENT

Non-Patent Document

Non-Patent Document 1: Dellepiane Matteo, et al. "Reconstructing head models from photographs for individualized 3D audio processing," Computer Graphics Forum. Vol. 27 NO. 7, Blackwell Publishing Ltd., 2008.

In the technique of Non-Patent Document 1, the head shape of the listener is estimated by moving (morphing) feature points that are extracted from images of the head of the listener, and there is a problem in that an unrealistic, collapsed head shape is estimated when an image process (e.g., extracting feature points) is not carried out appropriately. An inappropriate image process leads to a failure to estimate an ear shape with high precision.

SUMMARY OF THE INVENTION

In view of the above circumstances, an object of the present invention is to reduce a probability of misestimating an ear shape used in calculating head-related transfer functions.

In order to solve the problems described above, in one aspect, an ear shape analysis method is implemented by a computer, and the method includes: generating a first ear shape data set by applying a first principal component weight vector to an ear shape model reflecting statistical tendencies of three-dimensional shapes of ears; and identifying from the generated first ear shape data set an estimated three-dimensional shape of a target ear corresponding to a target ear image represented by image data.

In another aspect, an ear shape analysis device includes: an ear shape data generator configured to generate a first ear shape data set by applying a first principal component weight vector to an ear shape model reflecting statistical tendencies of three-dimensional shapes of ears; and an ear shape identifier configured to identify, from the first ear shape data set generated by the ear shape data generator, an estimated three-dimensional shape of a target ear corresponding to a target ear image represented by image data.

In still another aspect, an ear shape model generation method is implemented by a computer to generate an ear shape model used in generating a candidate ear image for comparison with a target ear image represented by image data, and the method includes: generating, for a plurality of sample ears, a plurality of ear shape data sets, each indicating a difference between a point group representing a three-dimensional shape of a corresponding sample ear and a point group representing a three-dimensional shape of a reference ear, and calculating a transformation matrix for translating ear shape data into a principal component weight vector indicating weights of principal components, by performing principal component analysis on the plurality of generated ear shape data sets, to generate the ear shape model including the transformation matrix or an inverse matrix of the transformation matrix.

DESCRIPTION OF THE EMBODIMENTS

First Embodiment

Figure 1:
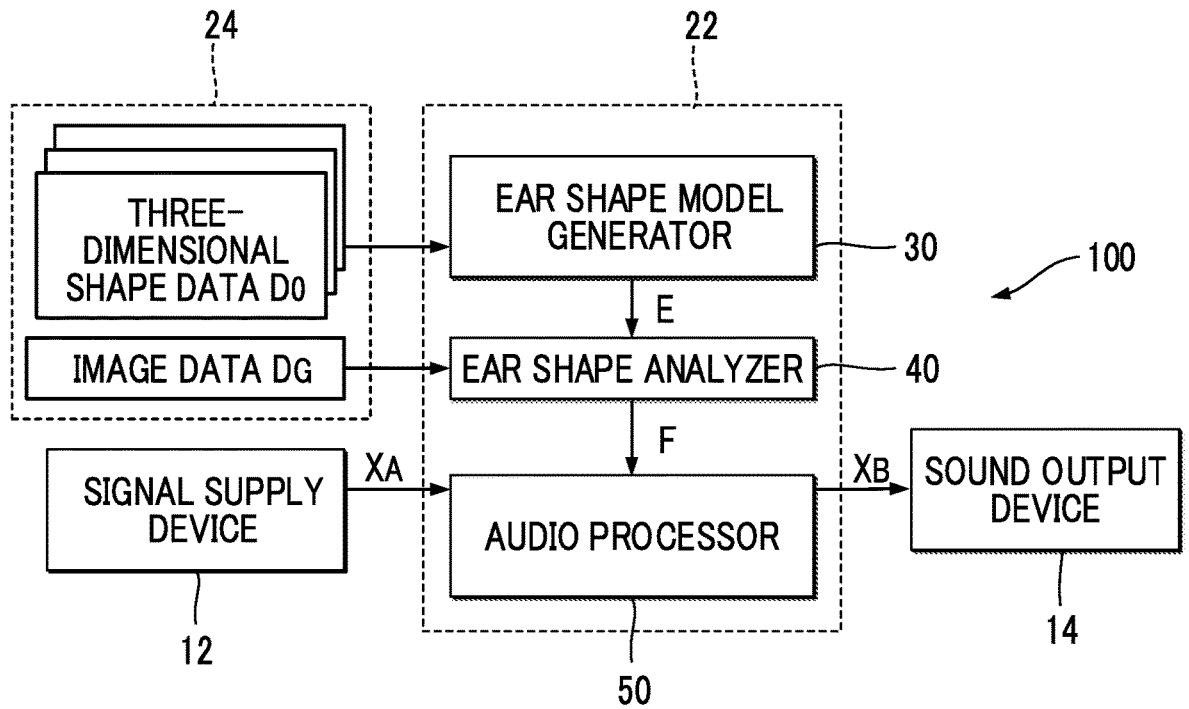
FIG. 1 is a block diagram showing a configuration of an audio processing device according to a first embodiment of the present invention.

FIG. 1 is a block diagram showing a configuration of an audio processing device 100 according to a first embodiment of the present invention. As shown in FIG. 1, a signal supply device 12 and a sound output device 14 are connected to the audio processing device 100 of the first embodiment. The signal supply device 12 supplies an audio signal $X_A$ representing a sound, such as a voice and a music sound, to the audio processing device 100. Specific examples of the signal supply device 12 include: a sound receiving device that receives a sound in the surroundings to generate an audio signal $X_A$; and a playback device that acquires an audio signal $X_A$ from a recording medium (either portable or in-built) and supplies the same to the audio processing device 100.

The audio processing device 100 is a signal processing device that generates an audio signal $X_B$ by applying audio processing to the audio signal $X_A$ supplied from the signal supply device 12. The audio signal $X_B$ is a stereo signal having two (left and right) channels. Specifically, the audio processing device 100 generates the audio signal $X_B$ by convolving a head-related transfer function (HRTF) F of a specific user (hereinafter, "subject") into the audio signal $X_A$. The sound output device 14 (headphones, earphones, etc.) is audio equipment, which is attached to both ears of a listener and outputs a sound that is in accordance with the audio signal $X_B$ generated by the audio processing device 100. A user listening to a playback sound output from the sound output device 14 is able to clearly perceive a location of a sound source of a sound component. For the sake of convenience, a D/A converter, which converts the audio signal $X_B$ generated by the audio processing device 100 from digital to analog, has been omitted from the drawings. Both or either one of the signal supply device 12 and the sound output device 14 may be mounted in the audio processing device 100.

As shown in FIG. 1, the audio processing device 100 is realized by a computer system including a control device 22 and a storage device 24. The storage device 24 stores therein a program executed by the control device 22 and various data used by the control device 22. A freely-selected form of well-known storage media, such as a semiconductor storage medium and a magnetic storage medium, or a combination of various types of storage media may be employed as the storage device 24. A configuration in which the audio signal $X_A$ is stored in the storage device 24 (accordingly, the signal supply device 12 may be omitted) is also preferable.

The control device 22 is an arithmetic unit (such as a central processing unit (CPU)), and by executing the program stored in the storage device 24, realizes different functions (an ear shape model generator 30, an ear shape analyzer 40, and an audio processor 50). A configuration in which the functions of the control device 22 are dividedly allocated to a plurality of devices, or a configuration which employs electronic circuitry that is dedicated to realize part of the functions of the control device 22, are also applicable.

The ear shape model generator 30 generates a statistical model (hereinafter, "ear shape model") E, which reflects statistical tendencies of shapes of a large number of ears that are prepared in advance as samples (hereinafter, "sample ears"). In the first embodiment, a case is assumed where the ear shape model E is generated with right ears being used as sample ears. The ear shape analyzer 40 estimates a shape of an ear of the subject (hereinafter, "target ear") using the ear shape model E generated by the ear shape model generator 30, and based on the estimated shape of the target ear, generates a head-related transfer function F from a given direction up to either ear hole of the subject. The audio processor 50 convolves the head-related transfer function F generated by the ear shape analyzer 40 into the audio signal $X_A$, so as to generate the audio signal $X_B$.

Details of elements realized by the control device 22 will be described below.

Ear Shape Model Generator 30

Figure 2:
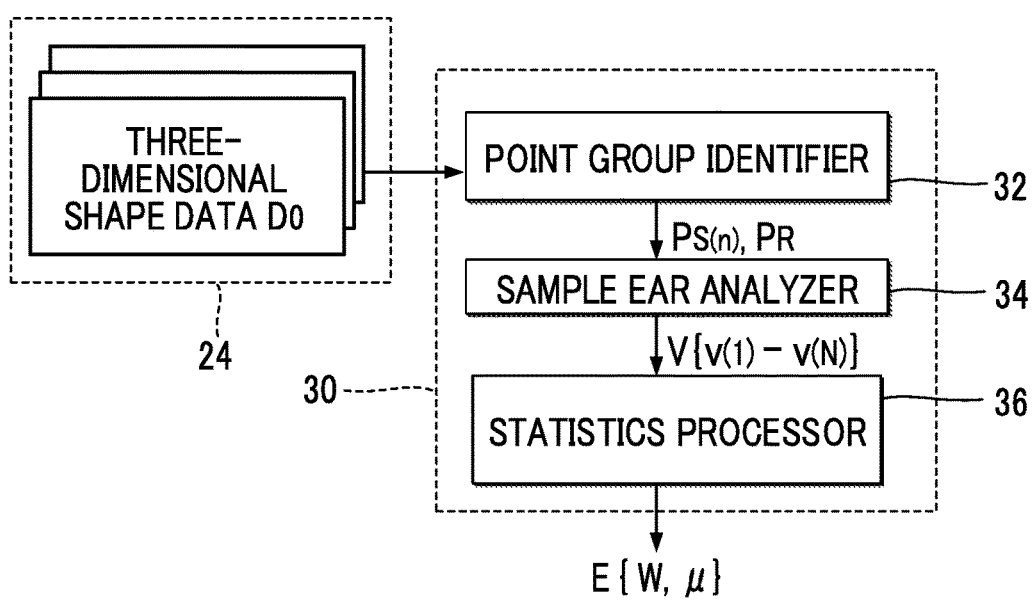
FIG. 2 is a block diagram showing a configuration of an ear shape model generator.

FIG. 2 is a block diagram showing a configuration of the ear shape model generator 30. As shown in FIG. 2, the storage device 24 of the first embodiment stores three-dimensional shape data $D_0$ for each of N sample ears (N is a natural number of 2 or more) and one ear prepared in advance (hereinafter, "reference ear"). For example, from among a large number of ears (e.g., right ears) of a large number of unspecified human beings for whom three-dimensional shapes of these ears were measured in advance, one specific ear is selected as the reference ear while the rest of the ears are selected as sample ears, and three-dimensional shape data $D_0$ is generated for each of the selected ears. Each three-dimensional shape data $D_0$ represents a three-dimensional shape of each of the sample ears and the reference ear. Specifically, polygon mesh data representing an ear shape in a form of a collection of polygons may preferably be used as the three-dimensional shape data $D_0$, for example. As shown in FIG. 2, the ear shape model generator 30 of the first embodiment includes a point group identifier 32, a sample ear analyzer 34, and a statistics processor 36.

The point group identifier 32 identifies a collection of multiple points (hereinafter, "point group") representing a three-dimensional shape of each sample ear and a point group representing a three-dimensional shape of the reference ear. The point group identifier 32 of the first embodiment identifies point groups $P_{S(n)}$ (n=1 to N) of the N sample ears from the respective three-dimensional shape data $D_0$ of the N sample ears, and identifies a point group $P_R$ of the reference ear from the three-dimensional shape data $D_0$ of the reference ear. Specifically, the point group identifier 32 identifies as a point group $P_{S(n)}$ a collection of vertices of the polygons that are designated by the three-dimensional shape data $D_0$ of an n-th sample ear from among the N sample ears, and identifies as the point group $P_R$ a collection of vertices of the polygons that are designated by the three-dimensional shape data $D_0$ of the reference ear.

Figure 3:
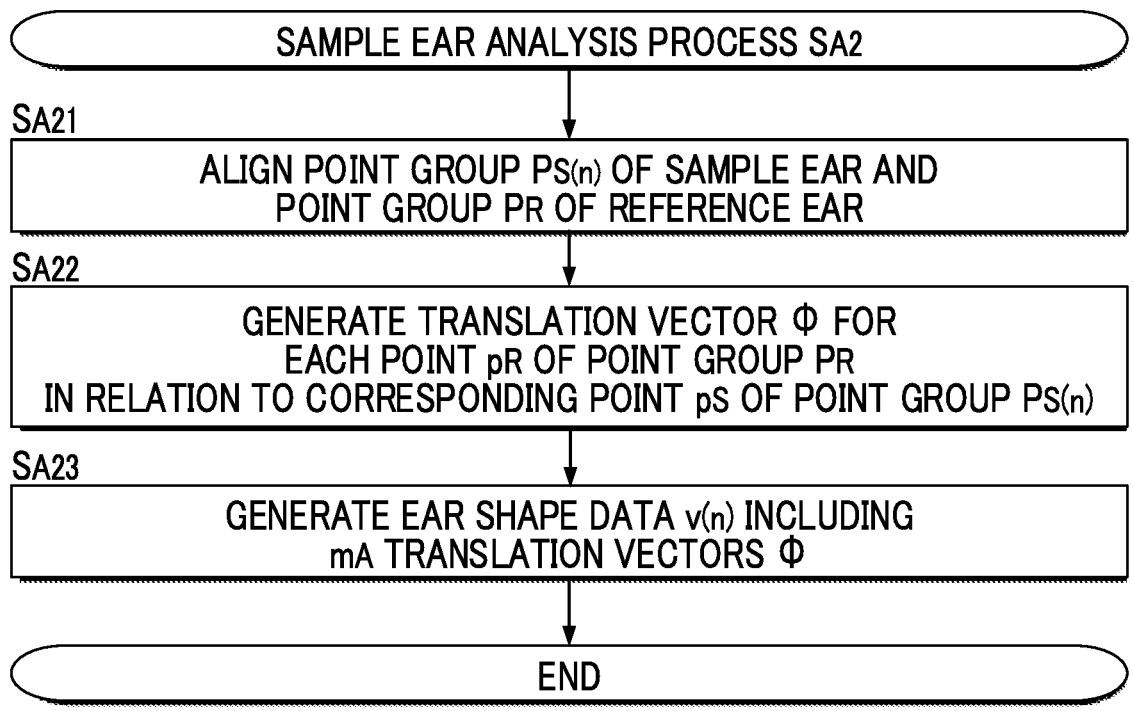
FIG. 3 is a flowchart showing a flow of a sample ear analysis process.

The sample ear analyzer 34 generates, for each of the N sample ears, ear shape data $v_{(n)}$ (one among ear shape data $v_{(1)}$ to $v_{(N)}$) indicating a difference between a point group $P_{S(n)}$ of a sample ear and the point group $P_R$ of the reference ear, the point groups $P_{S(n)}$ and $P_R$ having been identified by the point group identifier 32. FIG. 3 is a flowchart showing a flow of a process $S_{A2}$ for generating ear shape data $v_{(n)}$ of any one of the sample ears (hereinafter, "sample ear analysis process"), the process being executed by the sample ear analyzer 34. As a result of the sample ear analysis process $S_{A2}$ in FIG. 3 being executed for each of the N sample ears, N ear shape data $v_{(1)}$ to $v_{(N)}$ are generated.

Figure 4:
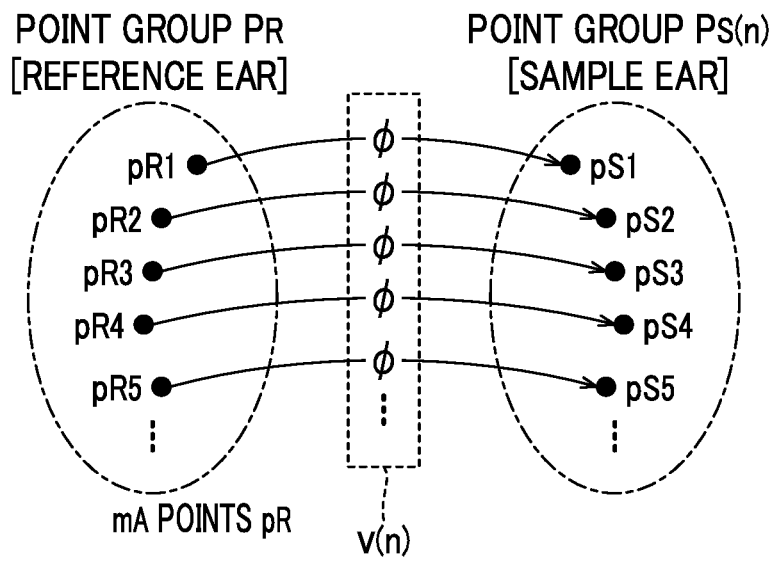
FIG. 4 is a diagram explaining the sample ear analysis process.

Upon start of the sample ear analysis process $S_{A2}$, the sample ear analyzer 34 performs point matching (associates) between a point group $P_{S(n)}$ of one sample ear to be processed and (with) the point group $P_R$ of the reference ear in three-dimensional space ($S_{A21}$). Specifically, for each of the plurality of points $p_R$ ($p_{R1}$, $p_{R2}$, . . . ) included in the point group $P_R$ of the reference ear, the sample ear analyzer 34 identifies a corresponding point $p_S$ ($p_{S1}$, $p_{S2}$, . . . ) in the point group $P_{S(n)}$, as shown in FIG. 4. For the point matching between a point group $P_{S(n)}$, and the point group $P_R$, a freely-selected one of publicly-known methods can be employed. Among the preferable methods is the method disclosed in Chui, Halil, and Anand Rangarajan, "A new point matching algorithm for non-rigid registration," Computer Vision and Image Understanding 89.2 (2003); 114-141, or the method disclosed in Jian, Bing, and Baba C. Vemuri, "Robust point set registration using Gaussian mixture models," Pattern Analysis and Machine Intelligence, IEEE Transaction on 33.8 (2011); 1633-1645.

As shown in FIG. 4, for each of $m_A$ points $p_R$ ($m_A$ is a natural number of 2 or more) constituting the point group $P_R$ of the reference ear, the sample ear analyzer 34 generates a vector $\varphi$ indicating a difference between each point $p_R$ and a corresponding point $p_S$ in a point group $P_{S(n)}$ of a sample ear ($S_{A22}$) (this vector will hereinafter be referred to as a "translation vector"). A freely selected translation vector $\varphi$ is a three-dimensional vector, elements of which are constituted by coordinate values of axes set in three-dimensional space. Specifically, a translation vector $\phi$ of a point $p_R$ in the point group $P_R$ expresses a location of a point $p_S$ of the point group $P_{S(n)}$ in three-dimensional space, based on the point $p_R$ serving as a point of reference. That is, as a result of a translation vector $\phi$ of a point $p_R$ in the point group $P_R$ being added to the point $p_R$, a point $p_S$ corresponding to the point $p_R$ in a point group $P_{S(n)}$ is reconstructed. Thus, a translation vector $\phi$ corresponding to a point $p_R$ in the point group $P_R$ of the reference ear may be expressed as a vector (warping vector) that serves to move or translate the point $p_R$ to another point (a point $p_S$ in a point group $P_{S(n)}$) corresponding to the point $p_R$.

The sample ear analyzer 34 generates ear shape data $v_{(n)}$ of a sample ear ($S_{A23}$), the ear shape data $v_{(n)}$ including $m_A$ translation vectors $\phi$ generated by the above procedure. Specifically, the ear shape data $v_{(n)}$ is an M-dimensional ($M=m_A\times3$) vector in which the three elements of a translation vector $\phi$ are arranged for each of the $m_A$ translation vectors $\phi$. As will be understood from the above description, for each of the N sample ears, there is generated ear shape data $v_{(n)}$ that indicates a difference between a point group $P_{S(n)}$ representing a three-dimensional shape of a freely selected sample ear and the point group $P_R$ representing the three-dimensional shape of the reference ear.

The statistics processor 36 in FIG. 2 calculates a transformation matrix W by performing principal component analysis on the N ear shape data $v_{(1)}$ to $v_{(N)}$ generated by the sample ear analyzer 34 in the sample ear analysis process $S_{A2}$ described above. The transformation matrix W, as expressed by equation (1) below, is a square matrix with M rows and M columns, which serves to translate ear shape data $v_{(n)}$ into a principal component weight vector $w_{(n)}$. A principal component weight vector $w_{(n)}$ is an M-dimensional vector, elements of which are respective weights of M principal components. The sign $\mu$ in equation (1) stands for a mean vector of the N ear shape data $v_{(1)}$ to $v_{(N)}$. The statistics processor 36 of the first embodiment generates an ear shape model E including the transformation matrix W and the mean vector $\mu$.

$$w(n)=W(v(n)-\mu) \quad (1)$$

Figure 5:
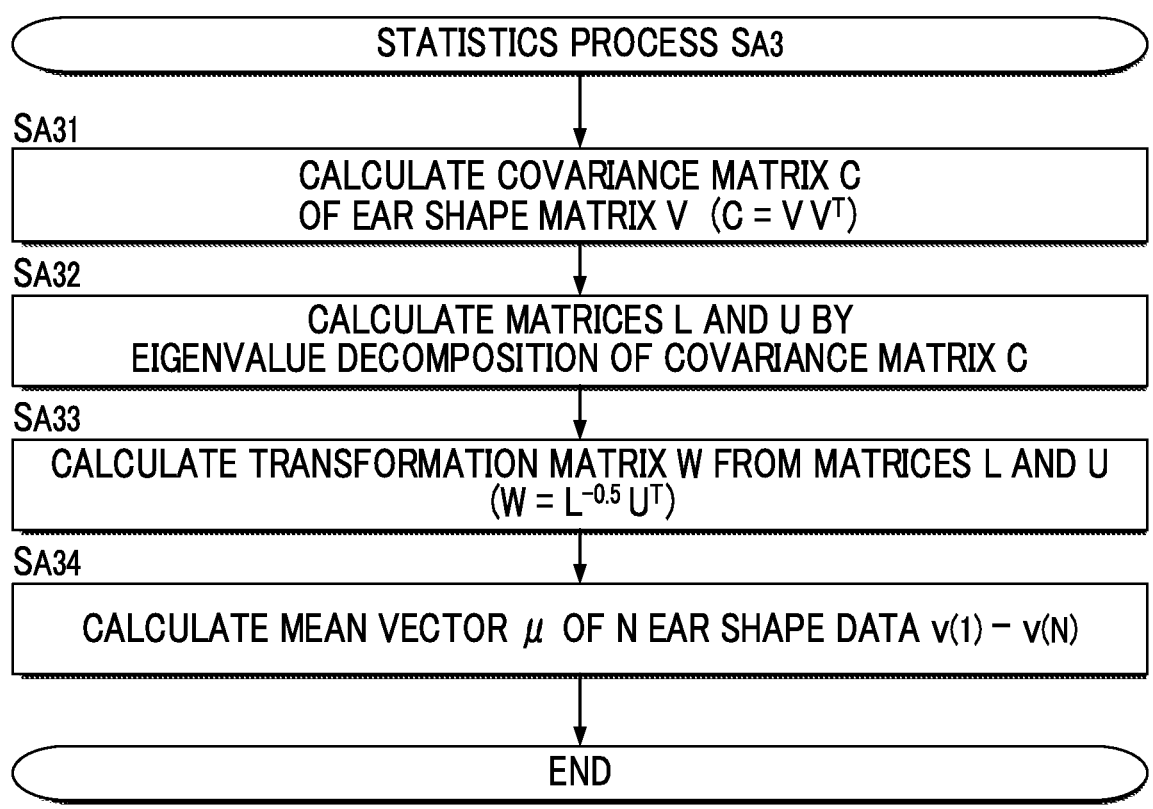
FIG. 5 is a flowchart showing a flow of a statistics process.

FIG. 5 is a flowchart showing a flow of a process $S_{A3}$ executed by the statistics processor 36 of the first embodiment, wherein the statistics processor 36 calculates the transformation matrix W by performing principal component analysis on the N ear shape data $v_{(1)}$ to $v_{(N)}$ (this process will hereinafter be referred to as a "statistics process"). The statistics process $S_{A3}$ shown in FIG. 5 is started by being triggered by the generation of the N ear shape data $v_{(1)}$ to $v_{(N)}$ by the sample ear analyzer 34.

By calculation of equation (2) below, the statistics processor 36 calculates a covariance matrix C of a matrix V in which the N ear shape data $v_{(1)}$ to $v_{(N)}$ generated by the sample ear analyzer 34 are arranged laterally, and which has M rows and N columns (the matrix V will hereinafter be referred to as an "ear shape matrix" V) ($S_{A31}$). The sign "T" in equation (2) stands for transpose of a matrix.

$$C=VV^T \quad (2)$$

The statistics processor 36 performs an eigenvalue decomposition expressed by equation (3) below on the covariance matrix C of the ear shape matrix V, thereby calculating matrices L and U ($S_{A32}$).

$$C=ULU^T \quad (3)$$

The statistics processor 36 calculates equation (4) below in which the matrices L and U calculated by calculation of equation (3) are used, thereby calculating a transformation matrix W ($S_{A33}$).

$$W=L^{-0.5}U^T \quad (4)$$

The statistics processor 36 calculates a mean vector $\mu$ of the N ear shape data $v_{(1)}$ to $v_{(N)}$ ($S_{A34}$). Above is a specific example of a statistics process $S_{A3}$ in which the statistics processor 36 calculates a transformation matrix W by performing principal component analysis on the N ear shape data $v_{(1)}$ to $v_{(N)}$ (ear shape matrix V).

Figure 6:
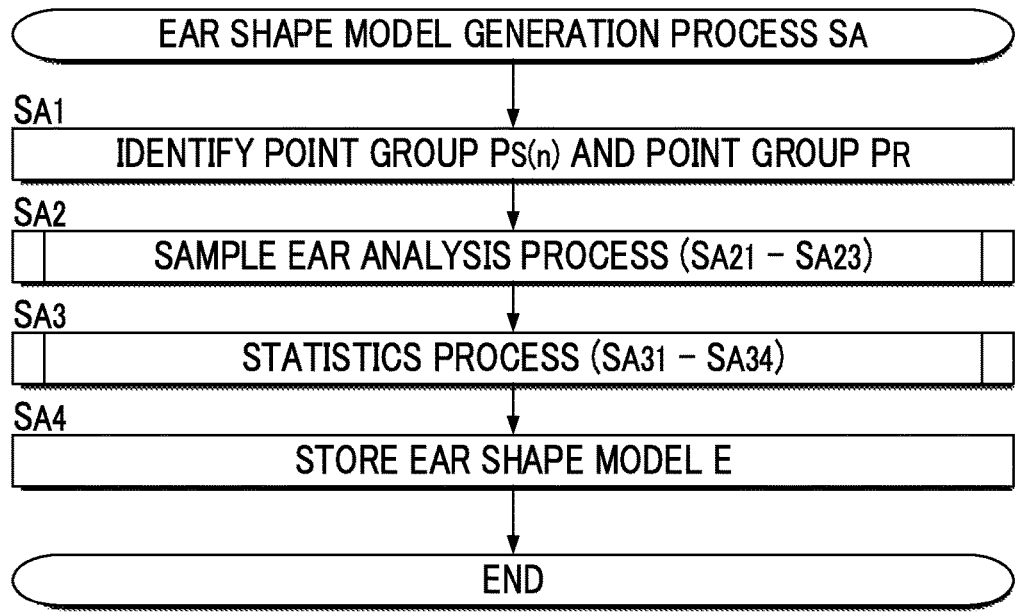
FIG. 6 is a flowchart showing a flow of an ear shape model generation process.

FIG. 6 is a flowchart showing a flow of a process $S_A$ for generating an ear shape model E (hereinafter, "ear shape model generation process"), the process being executed by the ear shape model generator 30 of the first embodiment described above. The ear shape model generation process $S_A$ in FIG. 6 is executed when, for example, an instruction is given by the user to generate the ear shape model E.

Upon start of the ear shape model generation process $S_A$, the point group identifier 32 identifies the point group $P_R$ of the reference ear and the point groups $P_{S(n)}$ ($P_{S(1)}$ to $P_{S(N)}$) of the N sample ears from the respective sets of three-dimensional shape data $D_0$ of the reference ear and the N sample ears ($S_{A1}$). By executing the sample ear analysis process $S_{A2}$ ($S_{A21}$ to $S_{A23}$) in FIG. 3, the sample ear analyzer 34 generates the N ear shape data $v_{(1)}$ to $v_{(N)}$ (each corresponding to a different sample ear) from the point group $P_R$ of the reference ear and the point groups $P_{S(n)}$ of the sample ears that have been identified by the point group identifier 32. The statistics processor 36 executes the statistics process $S_{A3}$ in FIG. 5, which includes the principal component analysis of the N ear shape data $v_{(1)}$ to $v_{(N)}$ generated by the sample ear analyzer 34 ($S_{A31}$ to $S_{A33}$), and thereby generates an ear shape model E including the transformation matrix W and the mean vector µ. The ear shape model E generated in the statistics process $S_{A3}$ is stored in the storage device 24 ($S_{A4}$). As a result of execution of the ear shape model generation process $S_A$ described above, the ear shape model E reflecting statistical tendencies of shapes of the N sample ears is generated. As will be understood from equation (1), the ear shape model E is a statistical model indicating a relation between ear shape data sets $v_{(n)}$ and a principal component weight vectors $w_{(n)}$.

Ear Shape Analyzer 40

Figure 7:
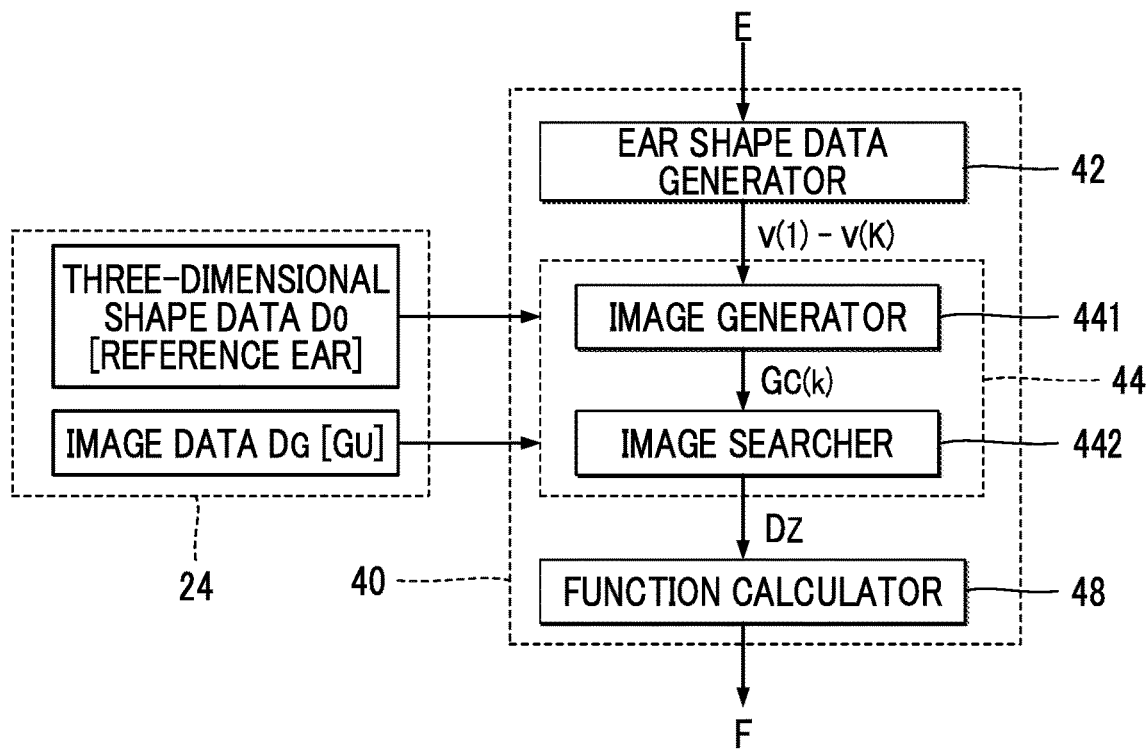
FIG. 7 is a block diagram showing a configuration of an ear shape analyzer.

Using the ear shape model E generated by the ear shape model generator 30, the ear shape analyzer 40 in FIG. 1 estimates a three-dimensional shape of the target ear of the subject, and based on the estimation result of the three-dimensional shape, generates a head-related transfer function F from a given direction up to either ear hole of the subject. FIG. 7 is a block diagram showing a configuration of the ear shape analyzer 40. As shown in FIG. 7, there is stored in the storage device 24 of the first embodiment image data $D_G$ representing an external appearance of the target ear of the subject. Specifically, under a prescribed condition (e.g., an angle of view or a direction of image capture), the subject (or an assistant present near the subject) captures an image of the target ear using an image-capturing device mounted in an information terminal, such as a portable telephone and a smartphone, or a dedicated image-capturing device, such as a digital still camera. The image of the target ear is captured in a state where an index of a magnification ratio of the image capture (for example, a sticker of a prescribed size) is attached to the target ear. Image data $D_G$ representative of an image $G_U$ of the target ear of the subject captured by the above method (hereinafter, "target ear image") is stored in the storage device 24. As shown in FIG. 7, the ear shape analyzer 40 of the first embodiment includes an ear shape data generator 42, an ear shape identifier 44, and a function calculator 48.

Figure 8:
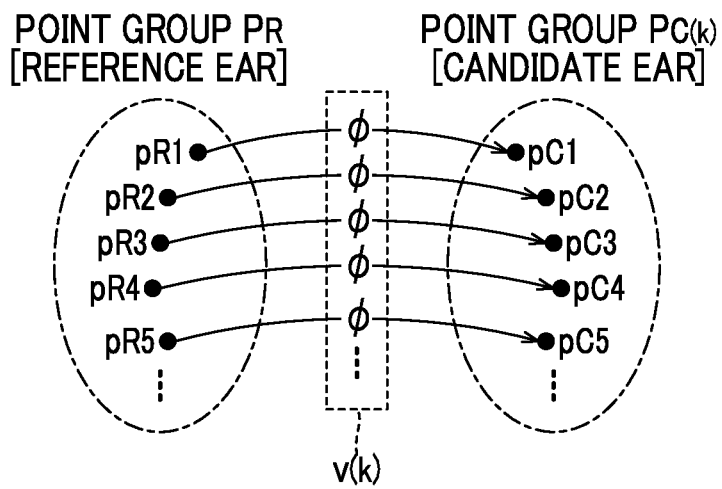
FIG. 8 is a diagram explaining an operation of an ear shape data generator.

Hereinafter, candidates for the target ear are referred to as "candidate ears". The ear shape data generator 42 generates ear shape data $v_{(k)}$ ($v_{(1)}$ to $v_{(K)}$) (K is a natural number of 2 or more) for each of the K different candidate ears. As shown in FIG. 8, ear shape data $v_{(k)}$ of a freely selected candidate ear indicates a difference between the point group $P_R$ of the reference ear and a point group $P_{C(k)}$ representing a three-dimensional shape of that candidate ear, as does the aforementioned ear shape data $v_{(n)}$ of the sample ear. Specifically, the ear shape data $v_{(k)}$ is an M-dimensional vector in which translation vectors φ are arranged for the respective $m_A$ points $p_R$ constituting the point group $P_R$ of the reference ear, each translation vector φ corresponding to a difference between each point $p_R$ ($p_{R1}$, $p_{R2}$, ...) in the point group $P_R$ of the reference ear and each point $p_C$ ($p_{C1}$, $p_{C2}$, ...) of a point group $P_{C(k)}$ of a candidate ear.

The ear shape data generator 42 of the first embodiment uses the ear shape model E (the transformation matrix W and the mean vector µ) generated by the ear shape model generator 30 and K principal component weight vectors $w_{(1)}$ to $w_{(K)}$ differing from each other, to generate ear shape data $v_{(1)}$ to $v_{(K)}$ for the K candidate ears. The principal component weight vector $w_{(k)}$ is an M-dimensional vector having the weights of the respective M principal components as elements thereof, similarly to the principal component weight vector $w_{(n)}$ of the above equation (1). Elements of a principal component weight vector $w_{(k)}$ of a candidate ear are set, for example, to random numbers within a prescribed range. However, a method of setting a principal component weight vector $w_{(k)}$ is not limited to the above example (random numbers). For example, numerical values distributed at equal intervals within a prescribed range may be employed as elements of a principal component weight vector $w_{(k)}$.

Specifically, the ear shape data generator 42 calculates ear shape data $v_{(k)}$ of a candidate ear by calculating equation (5) below in which equation (1) above is deformed (inverse operation of equation (1)). Specifically, the ear shape data generator 42 calculates ear shape data $v_{(k)}$ of a candidate ear by multiplying any one principal component weight vector $w_{(k)}$ by an inverse matrix $W^{-1}$ of the transformation matrix W and adding the resultant to the mean vector µ. As will be understood from the above description, similarly to equation (1), equation (5) expresses an ear shape model E indicating a relation between an ear shape data $v_{(n)}$ set and a principal component weight vector $w_{(n)}$. That is, equation (1) expresses an ear shape model E for generating a principal component weight vector $w_{(n)}$ from ear shape data $v_{(n)}$, whereas equation (5) expresses an ear shape model E for generating ear shape data $v_{(n)}$ from a principal component weight vector $w_{(n)}$.

$$v(k)=W^{-1}w(k)+\mu \qquad (5)$$

From the ear shape data $v_{(k)}$ generated by the ear shape data generator 42, the ear shape identifier 44 in FIG. 7 identifies a three-dimensional shape (hereinafter, "estimated three-dimensional shape") $Z_A$ of the target ear corresponding to the target ear image $G_U$ represented by the image data $D_G$. As shown in FIG. 7, the ear shape identifier 44 of the first embodiment includes an image generator 441 and an image searcher 442.

Figure 9:
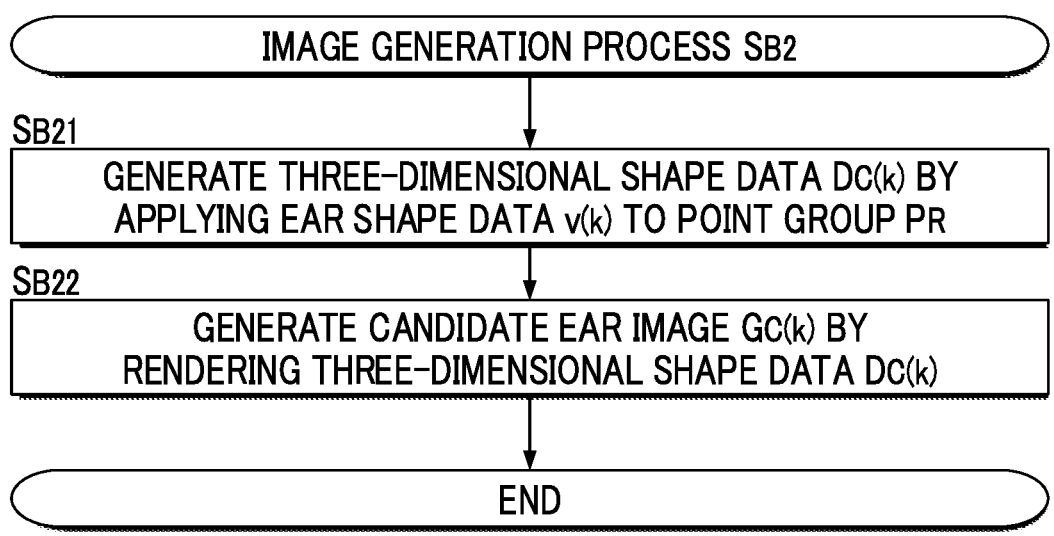
FIG. 9 is a flowchart showing a flow of an image generation process.

Based on the point group $P_R$ of the reference ear and the sets of ear shape data $v_{(k)}$ of the candidate ears generated by the ear shape data generator 42, the image generator 441 in FIG. 7 generates, for each k-th candidate ear of the K candidate ears, a candidate ear image $G_{C(k)}$ (one from among the candidate ear images $G_{C(1)}$ to $G_{C(K)}$) representing a corresponding candidate ear. FIG. 9 is a flowchart showing a flow of a process $S_{B2}$ for generating a candidate ear image $G_{C(k)}$ for a freely selected k-th candidate ear (hereinafter, "image generation process"), the process being executed by the image generator 441. K candidate ear images $G_{C(1)}$ to $G_{C(K)}$ are generated as a result of the image generation process $S_{B2}$ in FIG. 9 being executed for the respective K candidate ears.

As described with reference to FIG. 8, ear shape data $v_{(k)}$ of a freely selected candidate ear includes the $m_A$ translation vectors φ corresponding to the respective points $p_R$ of the point group $P_R$ of the reference ear. Upon start of the image generation process $S_{B2}$, the image generator 441 adds to coordinates of each of the $m_A$ points $p_R$ a translation vector φ corresponding to the point $p_R$ in the ear shape data $v_{(k)}$; the $m_A$ points $p_R$ being specified by the three-dimensional shape data $D_0$ of the reference ear. In this way, the image generator 441 generates three-dimensional shape data $D_{C(k)}$ representing a three-dimensional shape of each k-th candidate ear ($S_{B21}$).

The image generator 441 generates a candidate ear image $G_{C(k)}$ of each candidate ear by rendering the three-dimensional shape data $D_{C(k)}$ of each candidate ear ($S_{B22}$). Specifically, the candidate ear image $G_{C(k)}$ is an image obtained by observing the candidate ear, which is defined by the three-dimensional shape data $D_{C(k)}$ in three-dimensional space, from a viewpoint conforming to a certain condition. The "certain condition" means a condition (direction and angle of view) that approximates to the imaging condition of the target ear when the image of the target ear in the target ear image $G_U$ represented by the image data $D_G$ was captured. The K candidate ear images $G_{C(1)}$ to $G_{C(k)}$ corresponding to the principal component weight vectors $w_{(k)}$ differing from each other are generated as a result of the image generation process $S_{B2}$ illustrated above being executed for the respective ones of the K candidate ears. That is, K candidate ear images corresponding to K candidate ears having different shapes are generated.

The image searcher 442 in FIG. 7 compares the target ear image $G_U$ of the target ear represented by the image data $D_G$ with each of the K candidate ear images $G_{C(1)}$ to $G_{C(k)}$ generated by the image generator 441. Then, the image searcher 442 selects one candidate ear image from among K candidate ear images $G_{C(1)}$ to $G_{C(K)}$, and identifies the ear shape corresponding to the candidate ear of the selected one candidate ear image as an estimated three-dimensional shape $Z_A$ of the target ear. Specifically, the image searcher 442 selects a candidate ear image having the smallest difference $\varepsilon_{(k)}$ from the target ear image $G_U$. Specifically, using a known optimization technique (such as Bayesian optimization), the image searcher 442 of the first embodiment searches for a candidate ear corresponding a candidate ear image $G_{C(k)}$ having the smallest difference $\varepsilon_{(k)}$ from the target ear image $G_U$; and identifies the three-dimensional shape data $D_{C(k)}$ generated by the image generator 441 for that candidate ear in the image generation process $S_{B2}$ (step $S_{B21}$), as three-dimensional shape data $D_Z$ representing the estimated three-dimensional shape $Z_A$ of the target ear.

In comparing the target ear image $G_U$ with a candidate ear image $G_{C(k)}$, the target ear image $G_U$ is either enlarged or reduced such that the index of the magnification ratio included in the target ear image $G_U$ has a prescribed size. In this way, the size of the target ear in the target ear image $G_U$ and the size of a candidate ear in a candidate ear image $G_{C(k)}$ are adjusted to be substantially the same. A known image-comparison technique may be used to compare the target ear image $G_U$ and a candidate ear image $G_{C(k)}$. It is of note that preferably, an area in which the target ear is present is extracted from the target ear image $G_U$ and an area in which a candidate ear is present is extracted from a candidate ear image $G_{C(k)}$, and the two areas are thus compared with each other.

Figure 10:
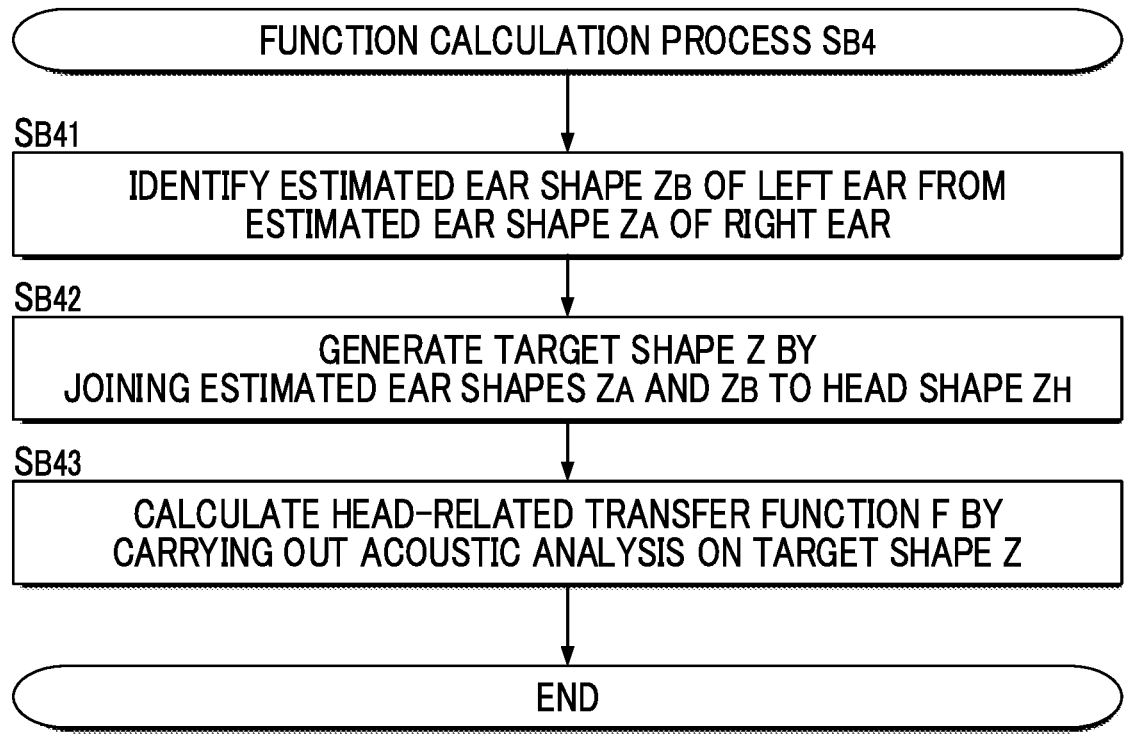
FIG. 10 is a flowchart showing a flow of a function calculation process.

The function calculator 48 in FIG. 7 calculates a head-related transfer function F of the subject, which corresponds to the estimated three-dimensional shape $Z_A$ of the target ear identified by the image searcher 442. The head-related transfer function F may be expressed as a head-related impulse response (HRIR) in a time domain. FIG. 10 is a flowchart showing a flow of a process $S_{B4}$ for calculating a head-related transfer function F (hereinafter, "function calculation process"), the process being executed by the function calculator 48. The function calculation process $S_{B4}$ is executed by being triggered by identification of an estimated three-dimensional shape $Z_A$ of the target ear performed by the image searcher 442.

Figure 11:
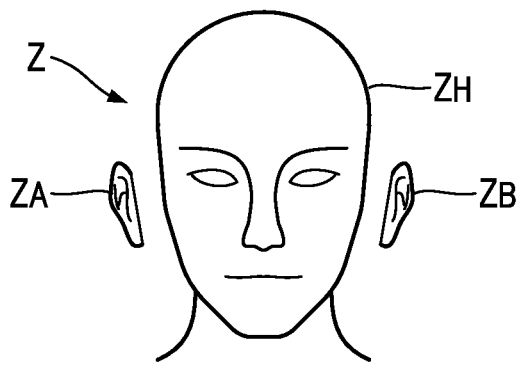
FIG. 11 is a diagram explaining a target shape used in calculating a head-related transfer function.

Upon start of the function calculation process $S_{B4}$, the function calculator 48 identifies an estimated three-dimensional shape $Z_B$ of the left ear of the subject from the estimated three-dimensional shape $Z_A$ of the target ear (right ear) identified by the image searcher 442 ($S_{B41}$), as shown in FIG. 11. Specifically, the function calculator 48 identifies, as the estimated three-dimensional shape $Z_B$ of the left ear, an ear shape that has a symmetrical relation to the estimated three-dimensional shape $Z_A$ represented by the three-dimensional shape data $D_Z$ of the target ear. Then, as shown in FIG. 11, the function calculator 48 joins the estimated three-dimensional shapes $Z_A$ and $Z_B$ to a head shape $Z_H$, and thereby identifies a shape Z of the entire head including the head and the ears ($S_{B42}$) (hereinafter, "target shape"). For example, the head shape $Z_H$ is a shape of a specific dummy head, or an average shape of heads of a large number of unspecified human beings.

The function calculator 48 calculates head-related transfer functions F by carrying out acoustic analysis on the target shape Z ($S_{B43}$). Specifically, the function calculator 48 of the first embodiment calculates, for each of the right ear and the left ear, a plurality of head-related transfer functions corresponding to different directions (different azimuth angles and different elevation angles) in which a sound arrives at the target shape Z. A known analysis method, such as a boundary element method and a finite element method, may be used to calculate head-related transfer functions F. For example, techniques, such as that disclosed in Katz, Brian F G. "Boundary element method calculation of individual head-related transfer function. I. Rigid model calculation." The Journal of the Acoustical Society of America 110.5 (2001): 2440-2448, may be used to calculate head-related transfer functions F corresponding to the target shape Z.

Figure 12:
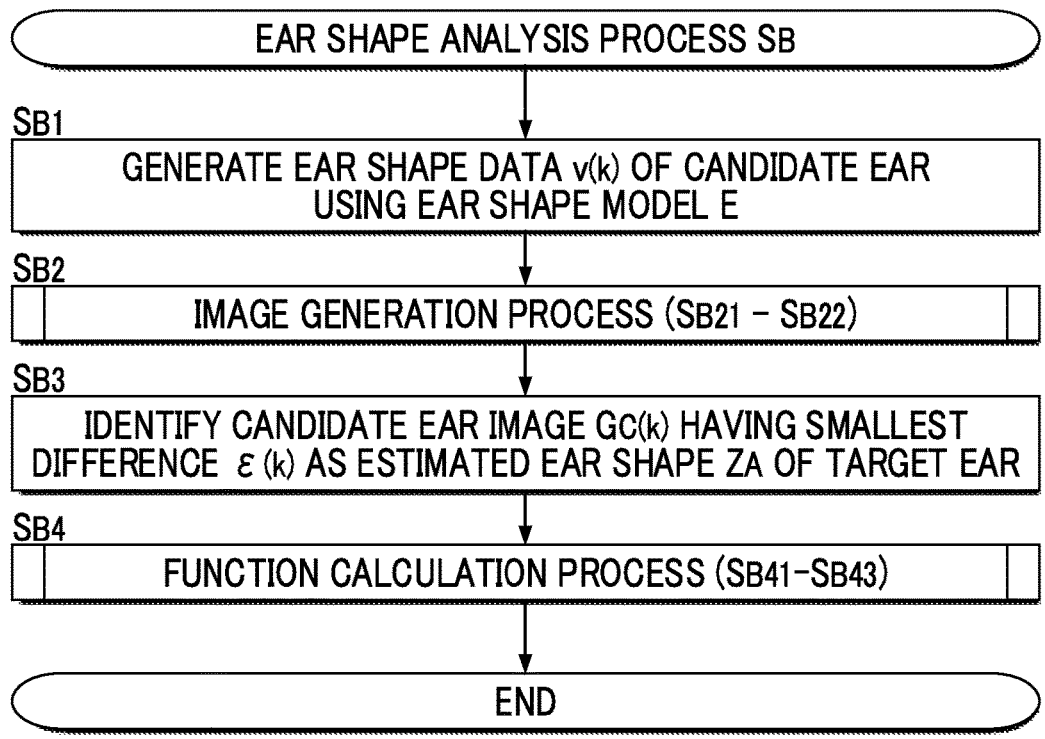
FIG. 12 is a flowchart showing a flow of an ear shape analysis process.

FIG. 12 is a flowchart showing a flow of a process $S_B$ for generating a head-related transfer function F (hereinafter, "ear shape analysis process"), the process being executed by the ear shape analyzer 40 of the first embodiment. The ear shape analysis process $S_B$ in FIG. 12 is executed when, for example, an instruction is given by the user to generate a head-related transfer function F after the ear shape model generator 30 has generated the ear shape model E.

Upon start of the ear shape analysis process $S_B$, the ear shape data generator 42 generates the ear shape data $v_{(1)}$ to $v_{(K)}$ of the K candidate ears, using the ear shape model E, and the K principal component weight vectors $w_{(1)}$ to $w_{(K)}$ ($S_{B1}$) differing from each other. Using the point group $P_R$ of the reference ear and the sets of ear shape data $v_{(k)}$ of the candidate ears generated by the ear shape data generator 42, the image generator 441 generates, for each k-th candidate ear of the K candidate ears, three-dimensional shape data $D_{C(k)}$ of a candidate ear image $G_{C(k)}$ (one among the candidate ear images $G_{C(1)}$ to $G_{C(K)}$) representing a corresponding candidate ear ($S_{B2}$). Then, the image searcher 442 identifies, as the estimated three-dimensional shape $Z_A$ of the target ear, an ear shape of a candidate ear image $G_{C(k)}$ having the smallest difference $\varepsilon_{(k)}$ from the target ear image $G_U$ represented by the image data $D_G$ ($S_{B3}$). By execution of the function calculation process $S_{B4}$ ($S_{B41}$ to $S_{B43}$) shown in FIG. 10, the function calculator 48 calculates head-related transfer functions F for the target shape Z of the entire head, the target shape Z including the estimated three-dimensional shape $Z_A$ identified by the image searcher 442. As a result of execution of the ear shape analysis process $S_B$ described above, head-related transfer functions F each reflecting an ear shape peculiar to the subject are generated, and the head-related transfer functions F are stored in the storage device 24.

Audio Processor 50

Figure 13:
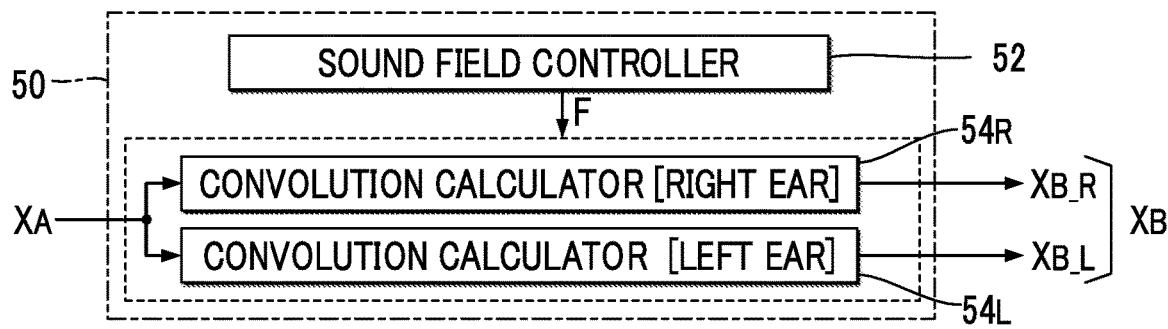
FIG. 13 is a block diagram showing a configuration of an audio processor.

The audio processor 50 in FIG. 1 convolves the head-related transfer function F generated by the ear shape analyzer 40 into the audio signal $X_A$, to generate the audio signal $X_B$. FIG. 13 is a block diagram showing a configuration of the audio processor 50. As shown in FIG. 13, the audio processor 50 of the first embodiment includes a sound field controller 52 and convolution calculators $54_R$ and $54_L$.

The user can instruct to the audio processing device 100 sound field conditions including a sound source location and a listening location in a virtual acoustic space. From a relation between the sound source location and the listening location, the sound field controller 52 calculates a direction in which a sound arrives to the listening location in the acoustic space. From among the multiple head-related transfer functions F calculated by the ear shape analyzer 40 and stored in the storage device 24, the sound field controller 52 selects for the respective ones of the left and right ears a head-related transfer function F corresponding to the direction in which the sound arrives at the listening location. By convolving into the audio signal $X_A$ the head-related transfer function F of the right ear selected by the sound field controller 52, the convolution calculator $54_R$ generates an audio signal $X_{B\_R}$ for a right channel By convolving into the audio signal $X_A$ the head-related transfer function F of the left ear selected by the sound field controller 52, the convolution calculator $54_L$ generates an audio signal $X_{B\_L}$ for a left channel. Convolution of the head-related transfer function F in a time domain (head-related impulse response) may be replaced by multiplication in a frequency domain.

In the first embodiment, as described above, each of the K principal component weight vectors $w_{(1)}$ to $w_{(K)}$ is applied to the ear shape model E so as to generate the ear shape data $v_{(1)}$ to $v_{(K)}$ of the K candidate ears, and the K candidate ear images $G_{C(1)}$ to $G_{C(K)}$ are generated in accordance with the point group $P_R$ of the reference ear and the ear shape data $v_{(k)}$ of the candidate ears. Then, from among the K candidate ear images $G_{C(1)}$ to $G_{C(K)}$, a search is made for a candidate ear image $G_{C(k)}$ that resembles the target ear image $G_U$ represented by the image data $D_G$. The shape of the candidate ear represented by the candidate ear image $G_{C(k)}$ found in the search is identified as the estimated three-dimensional shape $Z_A$ of the target ear. Accordingly, a probability of misestimating an ear shape can be reduced, compared to a configuration in which the shape of a target ear is estimated by deforming (morphing) a given shape. In the first embodiment, moreover, a head-related transfer function F that corresponds to the estimated three-dimensional shape $Z_A$ identified by the image searcher 442 is calculated. Consequently, an advantage is obtained in that it is possible to identify a head-related transfer function F, the use of which enables the subject to perceive an appropriate location of the sound image.

In the first embodiment, a candidate ear image $G_{C(k)}$ of a candidate ear observed from a viewpoint conforming to a condition approximate to the imaging condition of the target ear image $G_U$ is generated. Accordingly, an advantage is obtained in that a candidate ear having a shape that approximates to the shape of the target ear can be appropriately selected, compared to a case where observation conditions for a candidate ear image $G_{C(k)}$ do not match those used when the target ear image $G_U$ was captured.

In the first embodiment, the ear shape model E used in estimating the shape of the target ear reflects statistical tendencies of three-dimensional shapes of multiple sample ears. Thus, an advantage is obtained in that a three-dimensional shape of the target ear (estimated three-dimensional shape $Z_A$) can be estimated with high precision. Moreover, in the first embodiment, an ear shape model E that includes not only a transformation matrix W but also a mean vector μ is generated, and therefore, a candidate ear image $G_{C(k)}$ can be generated appropriately using the ear shape model E. Furthermore, the point groups $P_{S(n)}$ of the sample ears and the point group $P_R$ of the reference ear are identified from respective three-dimensional shape data $D_0$ representing three-dimensional shapes of the sample ears and the reference ear, and therefore, there is obtained an additional advantage in that these already available three-dimensional shape data $D_0$ (such as polygon mesh data) can be used to generate an ear shape model E.

Second Embodiment

A second embodiment of the present invention is described below. In the different embodiments described below, elements having substantially the same actions or functions as those in the first embodiment will be denoted by the same reference symbols as those used in the description of the first embodiment, and detailed description thereof will be omitted as appropriate.

In the sample ear analysis process $S_{A2}$ ($S_{A22}$) in the first embodiment, a translation vector φ is calculated for every point $p_R$ of the point group $P_R$ of the reference ear, in relation to each corresponding point $p_S$ of a sample ear. In the second embodiment, a translation vector φ is calculated for each of $m_A$ points $p_R$ constituting a part (hereinafter, "first group") of the point group $P_R$ of the reference ear, in relation to each corresponding point $p_S$ of a sample ear. In other words, while in the first embodiment the total number of the points $p_R$ constituting the point group $P_R$ of the reference ear is expressed as "$m_A$", the number "$m_A$" in the second embodiment means the number of points $p_R$ constituting the first group of the point group $P_R$ of the reference ear. As will be understood from the above description, ear shape data $v_{(n)}$ of a sample ear in the second embodiment includes $m_A$ translation vectors φ corresponding to the respective points $p_R$ constituting the first group of the point group $P_R$ of the reference ear.

Figure 14:
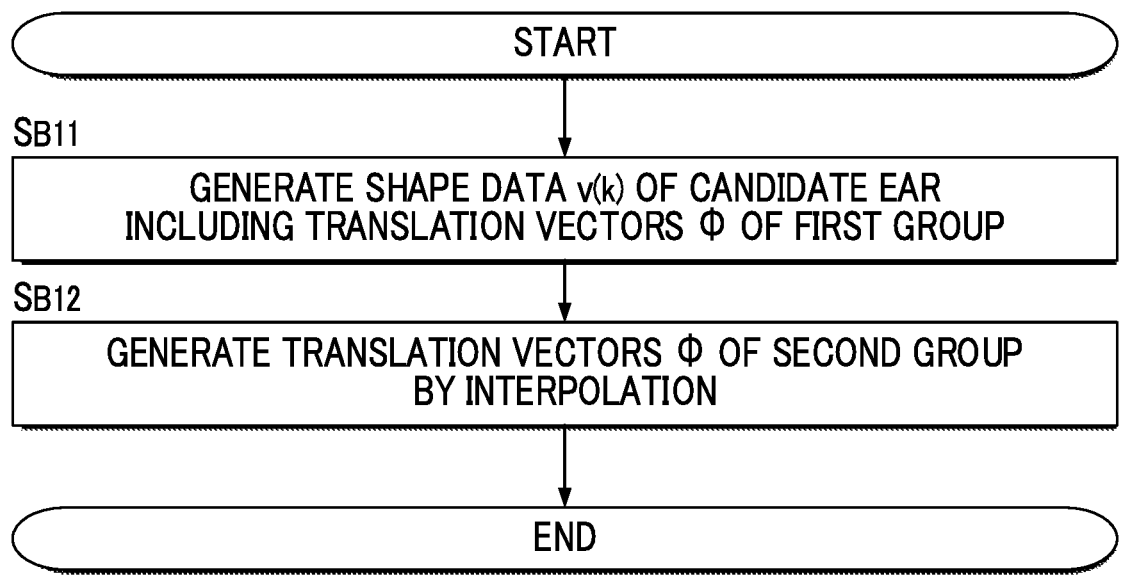
FIG. 14 is a flowchart showing a flow of an operation of the ear shape data generator according to a second embodiment.
Figure 15:
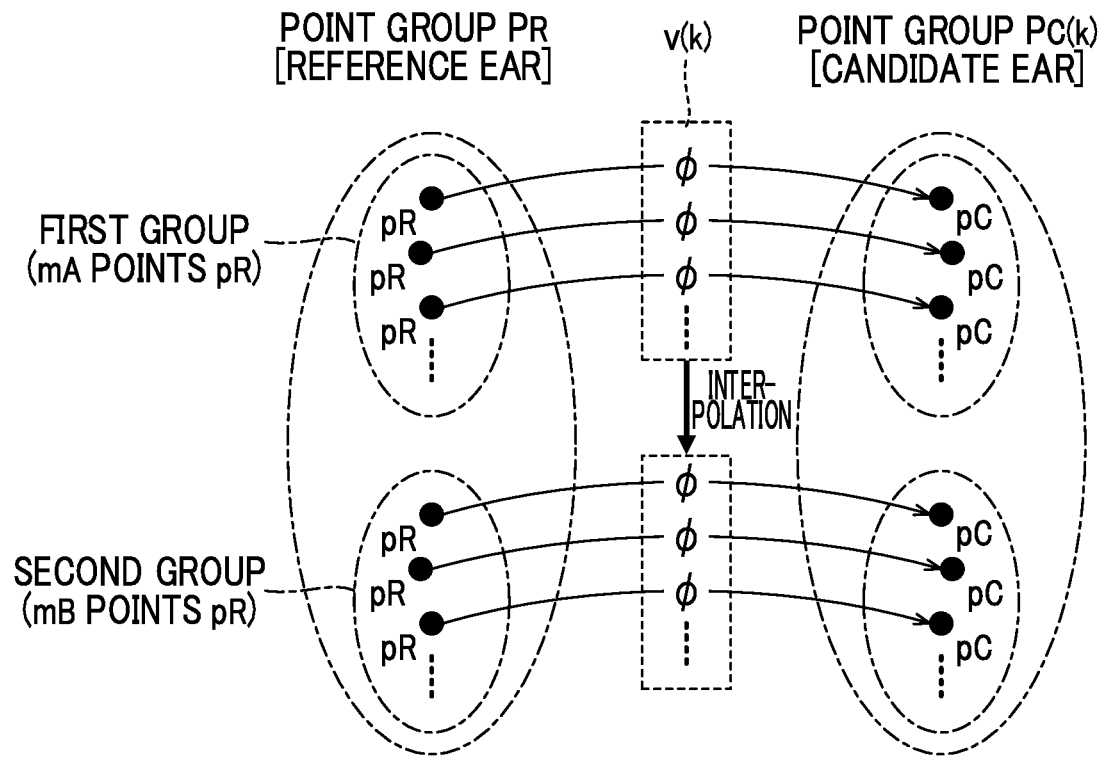
FIG. 15 is a diagram explaining an operation of the ear shape data generator according to the second embodiment.

FIG. 14 is a flowchart showing a flow of an operation of an ear shape data generator 42 of the second embodiment. FIG. 15 is a diagram explaining an operation of the ear shape data generator 42. The process in FIG. 14 is executed in step $S_{B1}$ of the ear shape analysis process $S_B$ shown in FIG. 12.

In substantially the same way as in the first embodiment, the ear shape data generator 42 applies a principal component weight vector $w_{(k)}$ of a candidate ear to an ear shape model E, and thereby generates ear shape data $v_{(k)}$ of the candidate ear ($S_{B11}$). In the second embodiment, the ear shape model E (a transformation matrix W and a mean vector μ) is generated by executing an ear shape model generation process $S_A$ that employs ear shape data $v_{(n)}$ of a sample ear including $m_A$ translation vectors φ corresponding to the respective points $p_R$ constituting the first group of the point group $P_R$ of the reference ear, as described above. Accordingly, ear shape data $v_{(k)}$ of a candidate ear generated by applying a principal component weight vector $w_{(k)}$ to the ear shape model E is constituted by the $m_A$ translation vectors φ corresponding to the respective points $p_R$ constituting the first group of the point group $P_R$ of the reference ear, as shown in FIG. 15. In other words, translation vectors φ of points $p_R$ constituting a group other than the first group (hereinafter, "second group", which is constituted by all points of the point group $P_R$ of the reference ear other than the points constituting the first group) are not generated by the process of applying a principal component weight vector $w_{(k)}$ to the ear shape model E, and are not included in ear shape data $v_{(k)}$ of a candidate ear.

Accordingly, the ear shape data generator 42 of the second embodiment generates $m_B$ translation vectors φ corresponding to the respective points $p_R$ constituting the second group of the point group $P_R$ of the reference ear by interpolation using the $m_A$ translation vectors φ included in the ear shape data $v_{(k)}$ of a candidate ear ($S_{B12}$). Specifically, a translation vector φ of a freely selected point (hereinafter, "specific point") $P_R$ in the second group of the point group $P_R$ of the reference ear is calculated, as expressed by equation (6) below, by calculating a weighted sum of translation vectors $\varphi_{(q)}$ (q=1 to Q (Q is a natural number of 2 or more)) of Q points $p_{R(1)}$ to $p_{R(Q)}$ among the $m_A$ points $p_R$ constituting the first group, the Q points $p_{R(1)}$ to $p_{R(Q)}$ being located in the proximity of the specific point $p_R$.

$$\phi = \sum_{q=1}^{Q} \frac{e^{-\alpha \cdot d^2(q)}}{\sum_{q=1}^{Q} e^{-\alpha \cdot d^2(q)}} \phi(q) \qquad (6)$$

In equation (6), the sign "e" is a base of a natural logarithm, and the sign "α" is a prescribed constant (positive number). The sign $d_{(q)}$ stands for a distance between a point $p_{R(q)}$ in the first group and the specific point $p_R$ (for example, a Euclidean distance). As will be understood from equation (6), a weighted sum of the Q translation vectors $\varphi_{(1)}$ to $\varphi_{(Q)}$, which is calculated by using weighted values corresponding to respective distances $d_{(q)}$ between the specific point $p_R$ and the respective points $p_{R(q)}$, is obtained as the translation vector $\varphi$ of the specific point $p_R$. As a result of the above process being executed by the ear shape data generator 42, a translation vector $\varphi$ is calculated for all ($m_A + m_B$) points $p_R$ of the reference ear. The number Q of points $p_{R(q)}$ in the first group that are taken into account in calculating the translation vector $\varphi$ of the specific point $p_R$ is typically set to a numerical value that is lower than the number $m_A$ of the points $p_R$ constituting the first group. However, the number Q of points $p_{R(q)}$ may be set to a numerical value corresponding to the number $m_A$ (that is, the translation vector $\varphi$ of the specific point $p_R$ may be calculated by interpolation of translation vectors $\varphi$ of all points $p_R$ belonging to the first group).

The process in which an image generator 441 generates a candidate ear image $G_{C(k)}$ using the translation vector $\varphi$ generated by the ear shape data generator 42 is substantially the same as that of the first embodiment. In step $S_{B21}$ of the image generation process $S_{B2}$ in FIG. 9, the image generator 441 translates the coordinates of each of $m_A$ points $p_R$ of the first group in the point group $P_R$ of the reference ear, by using a corresponding one of $m_A$ translation vectors $\varphi$ of the ear shape data $v_{(k)}$ of the candidate ear. Furthermore, the image generator 441 translates coordinates of each of the $m_B$ points $p_R$ constituting the second group of the point group $P_R$ of the reference ear, using a corresponding one of the $m_B$ translation vectors $\varphi$ having been obtained by the interpolation according to equation (6) (specifically, the translation vector $\varphi$ obtained by the interpolation is added to the coordinates of each point $p_R$). In this way, the ear shape data generator 42 generates three-dimensional shape data $D_{C(k)}$ of a candidate ear. The rest of the operation is substantially the same as that of the first embodiment.

Substantially the same effects as those of the first embodiment are obtained in the second embodiment. Furthermore, in the second embodiment, translation vectors $\varphi$ corresponding to the respective points $p_R$ constituting the second group of the point group $P_R$ of the reference ear are generated by interpolation of Q translation vectors $\varphi_{(1)}$ to $\varphi_{(Q)}$ included in ear shape data $v_{(k)}$ of a candidate ear. Thus, there is no need to generate translation vectors $\varphi$ for all points $p_R$ of the point group $P_R$ of the reference ear using the ear shape model E. According to the configuration described above, an advantage is obtained in that a load is reduced in a process executed by the ear shape data generator 42 to generate ear shape data $v_{(k)}$ of a candidate ear by applying a principal component weight vector $w_{(k)}$ to an ear shape model E, or in a process executed by the ear shape model generator 30 to generate an ear shape model E.

Third Embodiment

In the first embodiment, the statistics processor 36 generates a transformation matrix W with M rows and M columns. A statistics processor 36 of the third embodiment removes (a) prescribed row(s) from the lower rows of the transformation matrix W with M rows and M columns (that is, (a) prescribed row(s) corresponding to small eigenvalues), the transformation matrix W having been generated by performing principal component analysis on N ear shape data $v_{(1)}$ to $v_{(N)}$, and generates an ear shape model E including a transformation matrix W' that has been obtained by the removal and has M' rows and M columns (here, M'<M). Specifically, the statistical processor 36 deletes (M−M') rows from the (M'+1) th row to the Mth row in the matrix with M rows and M columns generated by the principal component analysis, and thereby obtains the transformation matrix W' with M' rows and M columns. Elements of rows from the first row to the M'th row are the same between the transformation matrix W and the transformation matrix W'.

An ear shape data generator 42 of the third embodiment generates ear shape data $v_{(1)}$ to $v_{(k)}$ of K candidate ears using the transformation matrix W' of the ear shape model E. Specifically, the ear shape data generator 42 generates a transformation matrix W with M rows and M columns by adding (M minus M') rows to the transformation matrix W' (elements of the (M minus M') rows having a prescribed value (e.g., zero)), and generates ear shape data $v_{(k)}$ of a candidate ear by calculation of equation (5) using the transformation matrix W obtained by the addition.

Substantially the same effects as those of the first embodiment are obtained in the third embodiment. Furthermore, in the third embodiment, a transformation matrix W' is generated for the ear shape model E, which transformation matrix W' is obtained by removing (a) prescribed row(s) from the lower rows of the transformation matrix W with M rows and M columns, the transformation matrix W having been generated by performing principal component analysis on N ear shape data $v_{(1)}$ to $v_{(K)}$ of sample ears. Thus, a data amount of the ear shape model E can be reduced. It is of note that the configuration of the second embodiment may be applied in the third embodiment.

Fourth Embodiment

Figure 16:
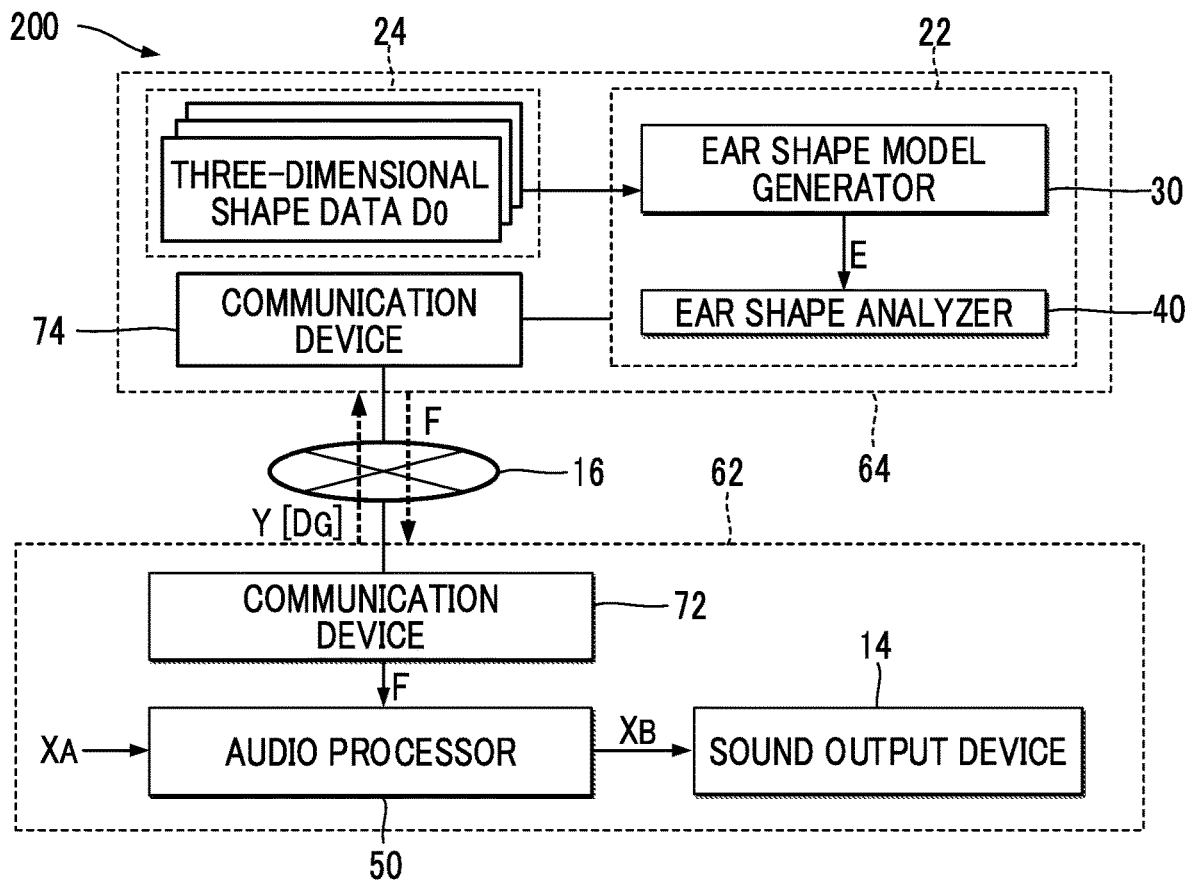
FIG. 16 is a block diagram showing a configuration of an audio processing system according to a fourth embodiment.

FIG. 16 is a block diagram showing a configuration of an audio processing system 200 according to a fourth embodiment. As shown in FIG. 16, the audio processing system 200 of the fourth embodiment is a computer system including a terminal device 62 and an analysis processing device 64. The terminal device 62 is an information processing device, such as a portable telephone, a smartphone, a tablet terminal, and a personal computer; and the analysis processing device 64 is, for example, a server device, such as a web server. In actuality, the audio processing system 200 includes multiple ones of the terminal device 62, but for the sake of convenience, the description below focuses on a freely selected, single terminal device 62.

The terminal device 62 includes an audio processor 50, a sound output device 14, and a communication device 72 (communicator). In substantially the same way as in the first embodiment, the audio processor 50 convolves a head-related transfer function F into an audio signal $X_A$ in order to generate an audio signal $X_B$, and the sound output device 14 outputs a sound that is in accordance with the audio signal $X_B$ generated by the audio processor 50. The communication device 72 communicates with the analysis processing device 64 via a communication network 16, such as a mobile communication network and the Internet. For example, the communication device 72 transmits to the analysis processing device 64 a distribution request Y for a head-related transfer function F. The distribution request Y includes image data $D_G$ of a target ear image $G_U$ captured of a target ear of the user (subject) of the terminal device 62. For example, image data $D_G$ of a target ear image $G_U$ captured using an image-capture function of the terminal device 62, or image data $D_G$ of a target ear image $G_U$ transmitted from an image-capturing device (e.g., a digital still camera) to the terminal device 62, may be transmitted from the terminal device 62 to the analysis processing device 64. Moreover, the distribution request Y includes sound field conditions designating a sound source location and a listening location in an acoustic space.

As shown in FIG. 16, the analysis processing device 64 includes an ear shape model generator 30, an ear shape analyzer 40, a storage device 24, and a communication device 74. The communication device 74 communicates with the terminal device 62 via the communication network 16. For example, the communication device 74 receives the distribution request Y transmitted from the terminal device 62. The storage device 24 stores multiple sets of three-dimensional shape data $D_0$ that are substantially the same as those in the first embodiment.

In substantially the same way as in the first embodiment, the ear shape model generator 30 generates an ear shape model E by executing the ear shape model generation process $S_A$ (FIG. 6) using multiple three-dimensional shape data $D_0$. The ear shape analyzer 40 executes the ear shape analysis process $S_B$ (FIG. 12) using the ear shape model E generated by the ear shape model generator 30 and the image data $D_G$ received by the communication device 74 from the terminal device 62, thereby generating head-related transfer functions F corresponding to the sound field conditions designated by the distribution request Y. The communication device 74 transmits the head-related transfer functions F generated by the ear shape analyzer 40 to the terminal device 62 that has transmitted the distribution request Y. Specifically, the head-related transfer functions F for the left and right ears, which correspond to the sound field conditions designated by the distribution request Y, are transmitted from the analysis processing device 64 to the terminal device 62.

The communication device 72 of the terminal device 62 receives the head-related transfer functions F transmitted from the analysis processing device 64. The audio processor 50 convolves each of the head-related transfer functions F received by the communication device 72 into the audio signal $X_A$ so as to generate the audio signal $X_B$. According to the above, the user (subject) of the terminal device 62 is enabled to perceive a location of a sound image of a sound that is played by the sound output device 14.

Substantially the same effects as those of the first embodiment are obtained in the fourth embodiment. Furthermore, in the fourth embodiment, an estimated three-dimensional shape $Z_A$ of the target ear is identified from image data $D_G$ received from the terminal device 62, and head-related transfer functions F corresponding to a target shape Z including the estimated three-dimensional shape $Z_A$ are calculated and delivered to the terminal device 62. Thus, an advantage is obtained in that there is no need to execute an ear shape model generation process $S_A$ or an ear shape analysis process $S_B$ (i.e., identification of an estimated three-dimensional shape $Z_A$ of the target ear, or calculation of head-related transfer functions F for the estimated three-dimensional shape $Z_A$) at each terminal device 62. It is of note that the configuration of the second embodiment or the third embodiment may be applied in the fourth embodiment.

Fifth Embodiment

Figure 17:
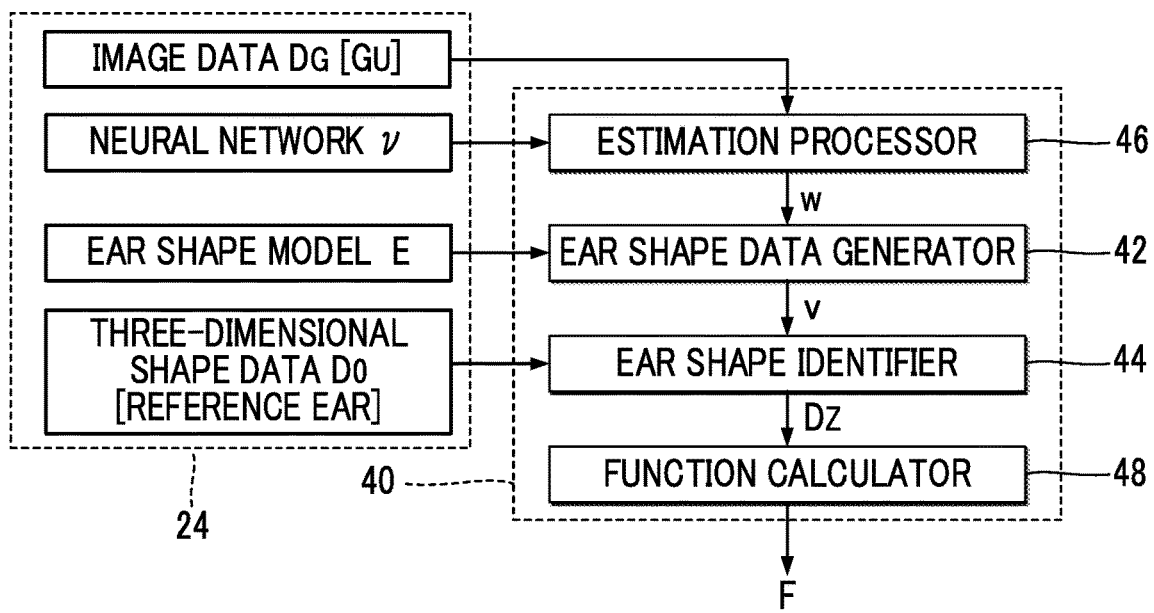
FIG. 17 is a block diagram showing a configuration of the ear shape analyzer according to a fifth embodiment.

FIG. 17 is a block diagram showing a configuration of an ear shape analyzer 40 according to a fifth embodiment. The ear shape analyzer 40 of the fifth embodiment includes an estimation processor 46, an ear shape data generator 42, an ear shape identifier 44, and a function calculator 48. In substantially the same way as in the first embodiment, image data $D_G$ representing a target ear image $G_U$, an ear shape model E (a transformation matrix W and a mean vector μ), and three-dimensional shape data $D_0$ of the reference ear are stored in a storage device 24. The image data $D_G$ in the fifth embodiment represents multiple target ear images $G_U$ in which the same target ear is captured from different angles.

The estimation processor 46 applies the target ear image $G_U$ represented by the image data $D_G$ to a neural network v, so as to generate a principal component weight vector w of the target ear. The neural network v is a mathematical model indicating a relation between ear images and principal component weight vectors w, and is generated by machine learning using a large amount of learning data including ear images of sample ears and principal component weight vectors of the sample ears.

Figure 18:
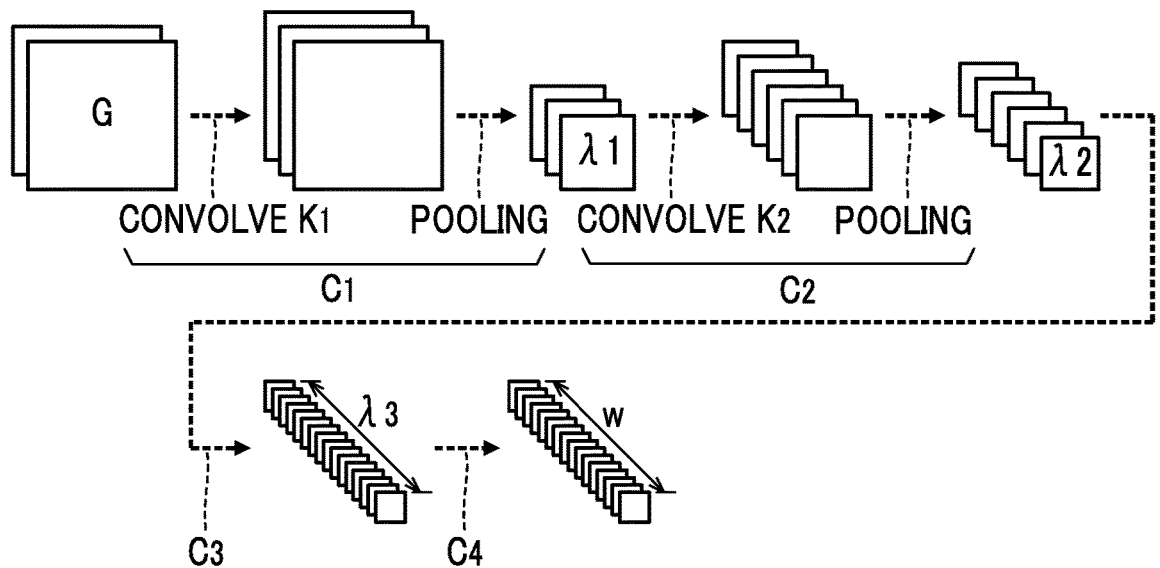
FIG. 18 is a diagram explaining a neural network used in the fifth embodiment.

FIG. 18 is a diagram explaining a neural network v used by the estimation processor 46. Multiple feature maps $λ_1$ are generated by performing an arithmetic processing operation $C_1$ on multiple ear images G of an ear that have been captured from different angles. The arithmetic processing operation $C_1$ is expressed by equation (7a) below. The sign "Conv(G,$K_1$)" in expression (7a) stands for calculation of convolving a convolution kernel $K_1$ into each of the multiple ear images G and adding up the results of convolution. The sign "$b_1$" is a vector indicative of a compensation term (bias), and the sign "tanh" is a hyperbolic tangent function. The sign "Pool" in equation (7a) is a maximum pooling function for reducing the image subject to the arithmetic processing by selecting the maximum value of a plurality of pixel values in each of rectangular areas obtained by dividing the image subject to the arithmetic processing. As a result of carrying out the arithmetic processing operation $C_1$ of equation (7a) using convolution kernels $K_1$ differing from each other, multiple (three in the illustration of FIG. 18) feature maps $λ_1$ are generated. In the above description, the arithmetic processing operation $C_1$ is carried out on the multiple ear images G captured from different angles; however, the arithmetic processing operation $C_1$ may be carried out on a single ear image in which an ear is captured from one specific angle.

$$λ_1 = \text{Pool}(\tanh(\text{Conv}(G, K_1) + b_1)) \quad (7a)$$

An arithmetic processing operation $C_2$ is carried out on the multiple feature maps $λ_1$ having been generated in the arithmetic processing operation $C_1$, and multiple feature maps $λ_2$ are generated as a result. The arithmetic processing operation $C_2$ is expressed by equation (7b) below. The sign "Conv($λ_1$,$K_2$)" in expression (7b) stands for calculation of convolving a convolution kernel $K_2$ into each of the multiple feature map $\lambda_1$ and adding up the results of convolution. The sign "$b_2$" is a vector indicative of a compensation term. As a result of carrying out the arithmetic processing operation $C_2$ of equation (7b) using convolution kernels $K_2$ differing from each other, multiple (six in the illustration of FIG. 18) feature maps $\lambda_2$ are generated.

$$\lambda_2 = \text{Pool}(\tan h(\text{Conv}(\lambda_1, K_2) + b_2)) \quad (7b)$$

An arithmetic processing operation $C_3$ is carried out on the multiple feature maps $\lambda_2$ having been generated in the arithmetic processing operation $C_2$, and connection vectors $\lambda_3$ are generated as a result. The arithmetic processing operation $C_3$ is a full-connection processing operation that is expressed by equation (7c) below. The sign "$\Omega_3$" in equation (7c) is a connection coefficient matrix (specifically, a matrix, elements of which are weighted values of multiple connection vectors $\lambda_3$), and the sign "$b_3$" is a vector indicative of a compensation term.

$$\lambda_3 = \tan h(\Omega_3 \lambda_2 + b_3) \quad (7c)$$

An arithmetic processing operation $C_4$ is carried out on the connection vectors $\lambda_3$ having been generated in the arithmetic processing operation $C_3$, and a principal component weight vector w is generated as a result. The arithmetic processing operation $C_4$ is expressed by equation (7d) below. The sign "$\Omega_4$" is a connection coefficient matrix.

$$w = \Omega_4 \lambda_3 \quad (7d)$$

The variables ($b_1$, $b_2$, $b_3$, $K_1$, $K_2$, $\Omega_3$, and $\Omega_4$) used in the processing operations above define the neural network v. Before the arithmetic processing operations are carried out, numerical values of the variables defining the neural network v are set using machine learning and are stored in the storage device 24. The estimation processor 46 of the fifth embodiment carries out, on the target ear image $G_U$, the arithmetic processing operations $C_1$ to $C_4$ in which the numerical values stored in the storage device 24 are used, to thereby generate a principal component weight vector w of the target ear. Generation of the neural network v by machine learning will be described later.

The ear shape data generator 42 in FIG. 17 applies to the ear shape model E the principal component weight vector w of the target ear generated by the estimation processor 46, and thereby generates ear shape data v of the target ear. Specifically, in substantially the same way as with equation (5) above, the ear shape data generator 42 multiplies the principal component weight vector w estimated by the estimation processor 46 by an inverse matrix $W^{-1}$ of the transformation matrix W and adds to the resultant a mean vector μ, thereby calculating ear shape data v of the target ear. The ear shape data v of the target ear is an M-dimensional vector indicating a difference between the point group $P_R$ of the reference ear and a point group representing a three-dimensional shape of the target ear. As will be understood from the above description, in the fifth embodiment there is calculated single ear shape data v corresponding to a principal component weight vector w generated from the target ear image $G_U$, whereas in the first embodiment there are calculated K ear shape data $v_{(1)}$ to $v_{(k)}$ each corresponding to a different candidate ear.

The ear shape identifier 44 identifies an estimated three-dimensional shape $Z_A$ of the target ear from the ear shape data v generated by the ear shape data generator 42. Specifically, in accordance with the ear shape data v of the target ear, the ear shape identifier 44 moves points $p_R$ of the point group $P_R$ specified by the three-dimensional shape data $D_0$ of the reference ear, and thereby identifies three-dimensional shape data $D_Z$ representing the three-dimensional shape of the target ear. That is, for each point of the $m_A$ points $p_R$ of the point group $P_R$ of the reference ear, the translation vector φ corresponding to that point in the ear shape data v of the target ear is added to the coordinates of that point. In this way, three-dimensional shape data $D_Z$ of the target ear is generated.

The function calculator 48 in FIG. 17 calculates a head-related transfer function F of the subject, which corresponds to the estimated three-dimensional shape $Z_A$ of the target ear identified by the ear shape identifier 44. A method of calculating a head-related transfer function F from the estimated three-dimensional shape $Z_A$, and a method of generating an audio signal $X_B$ from an audio signal $X_A$ using a head-related transfer function F are substantially the same as those of the first embodiment.

Figure 19:
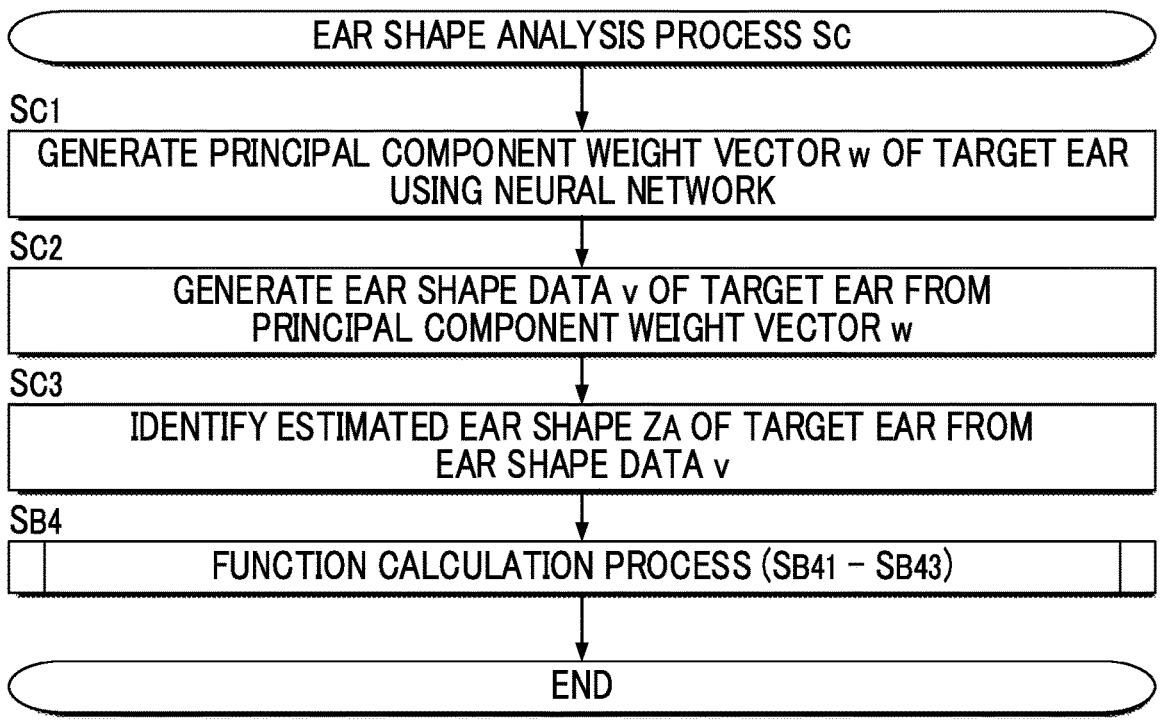
FIG. 19 is a flowchart showing a flow of the ear shape analysis process according to the fifth embodiment.

FIG. 19 is a flowchart showing a flow of an ear shape analysis process $S_C$ executed by the ear shape analyzer 40 of the fifth embodiment to generate a head-related transfer function F. The ear shape analysis process $S_C$ in FIG. 19 is executed when, for example, an instruction is given by the user to generate a head-related transfer function F.

Upon start of the ear shape analysis process $S_C$, the estimation processor 46 applies the target ear image $G_U$ represented by the image data $D_G$ to the neural network v, and thereby generates a principal component weight vector w of the target ear ($S_{C1}$). The ear shape data generator 42 applies the principal component weight vector w of the target ear generated by the estimation processor 46 to the ear shape model E, and thereby generates ear shape data v of the target ear ($S_{C2}$). The ear shape identifier 44 identifies an estimated three-dimensional shape $Z_A$ of the target ear from the ear shape data v generated by the ear shape data generator 42 ($S_{C3}$). By execution of the function calculation process $S_{B4}$ ($S_{B41}$ to $S_{B43}$) shown in FIG. 10, the function calculator 48 calculates head-related transfer functions F for a target shape Z of the entire head ($S_{B4}$), the target shape Z including the estimated three-dimensional shape $Z_A$ of the target ear identified by the ear shape identifier 44.

As described above, in the fifth embodiment, ear shape data v of the target ear is generated by applying a principal component weight vector w to an ear shape model E, and an estimated three-dimensional shape $Z_A$ of the target ear is identified from the ear shape data v. Accordingly, in substantially the same way as in the first embodiment, a probability of misestimating an ear shape can be reduced, compared to a configuration in which the shape of a target ear is estimated by deforming (morphing) a given shape.

In the first embodiment, the ear shape of the candidate ear, for which the difference $\varepsilon_{(k)}$ between the target ear image $G_U$ and each of the K candidate ear images $G_{C(k)}$ respectively corresponding to the K candidate ears is the smallest, is searched for as the estimated three-dimensional shape $Z_A$ of the target ear. In the first embodiment, therefore, it is necessary that generation of a candidate ear image $G_{C(k)}$ (image generation process $S_{B2}$) as well as comparison of a candidate ear image $G_{C(k)}$ with the target ear image $G_U$ (calculation of a difference $\varepsilon_{(k)}$) be performed repeatedly for K candidate ears. In the fifth embodiment, on the other hand, ear shape data v of the target ear is generated by applying, to the ear shape model E, a principal component weight vector w of the target ear identified from the target ear image $G_U$. Thus, there is no need to repeat generation of a candidate ear image $G_{C(k)}$ and comparison of a candidate ear image $G_{C(k)}$ with the target ear image $G_U$. As will be understood from the above description, an advantage is obtained in the fifth embodiment in that an amount of calculation necessary for the ear shape analyzer 40 to identify an estimated three-dimensional shape $Z_A$ of the target ear is reduced, compared to the first embodiment.

The neural network v may include a process to normalize (hereinafter, "normalization process") the principal component weight vector w of the target ear generated in the process of step $S_{C1}$ mentioned above. That is, a normalization layer may be added to the uppermost layer of the neural network v. The normalization process serves to divide each of M elements constituting the principal component weight vector w by a standard deviation of the M elements. The principal component weight vector w having undergone the normalization process (that is, a principal component weight vector w generated by the neural network v) is applied to the ear shape model E as in the example given above ($S_{C2}$). Here, an advantage is obtained in that, as a result of executing the normalization process described above, a probability of estimating an excessively anomalous principal component weight vector w (and in turn an excessively anomalous estimated three-dimensional shape $Z_A$ of the target ear) can be reduced.

Figure 20:
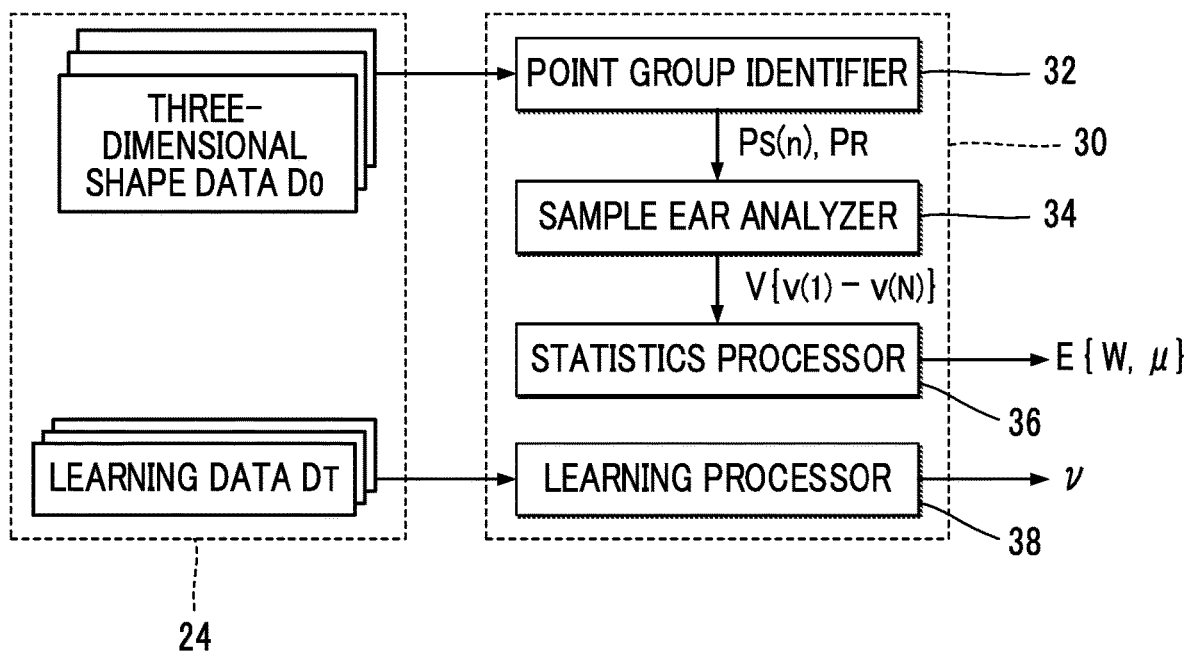
FIG. 20 is a block diagram showing a configuration of the ear shape model generator according to the fifth embodiment.

FIG. 20 is a block diagram showing a configuration of an ear shape model generator 30 of the fifth embodiment. As shown in FIG. 20, the ear shape model generator 30 of the fifth embodiment includes a learning processor 38 in addition to elements for generating an ear shape model E (a point group identifier 32, a sample ear analyzer 34, and a statistics processor 36) that are substantially the same as those in the first embodiment. Through machine learning, the learning processor 38 determines numerical values for the variables of the neural network v that are used by the estimation processor 46 to generate the principal component weight vector w.

Multiple sets of learning data $D_T$ stored in the storage device 24 are used in the machine learning performed by the learning processor 38. Each learning data $D_T$ includes an ear image G of a sample ear and an already-known principal component weight vector w of that ear image G. The learning processor 38 determines numerical values for the variables ($b_1$, $b_2$, $b_3$, $K_1$, $K_2$, $\Omega_3$, and $\Omega_4$) defining the neural network v such that, according to these numerical values, a vector calculated by applying an ear image G of a sample ear to the neural network v approximates to the already known principal component weight vector w of that ear image G. The numerical values of the variables determined by the learning processor 38 are stored in the storage device 24 and, as described above, used in generation of a principal component weight vector w (arithmetic processing operations $C_1$ to $C_4$) by the estimation processor 46.

Specifically, the learning processor 38 determines the numerical value of each variable of the neural network v so that the error function δ defined by equation (8) below is minimized.

$$\delta = |w\_est - w\_truth|_2 + \delta\_reg \qquad (8)$$

The sign "| |$_2$" in equation (8) stands for a 2-norm (Euclidean norm). The sign "w_est" is a principal component weight vector w calculated by applying an ear image G of a sample ear to the neural network v, and the sign "w_truth" is a principal component weight vector w (correct solution) included in the learning data $D_T$. As will be understood from equation (8), numerical values of the variables of the neural network v are determined such that a difference is minimized between the principal component weight vector w_est calculated by the neural network v from the ear image G in the learning data $D_T$ and the principal component weight vector w_truth included in the learning data $D_T$.

The sign "δ_reg" in equation (8) is a regularization term serving to improve precision in the machine learning, and may be defined by equation (9) below, for example.

$$\delta\_reg = \beta_1(\mathrm{mean}(w\_est**2) - \beta_2)^2 + \beta_3(\mathrm{mean}(w\_est) - \beta_4)^2 \qquad (9)$$

The "mean(x)" in equation (9) stands for a mean of multiple elements of a vector x, and the sign "x**2" stands for a vector obtained by squaring each element of the vector x. The signs "$\beta_1$" to "$\beta_4$" are prescribed real numbers.

A configuration substantially the same as that of the second embodiment may be employed in the fifth embodiment. Specifically, in the fifth embodiment, translation vectors φ corresponding to the respective points $p_R$ constituting the second group of the point group $P_R$ of the reference ear may be generated by interpolation of Q translation vectors $\varphi_{(1)}$ to $\varphi_{(Q)}$ included in the ear shape data $v_{(k)}$ of the target ear generated by the ear shape data generator 42. Moreover, the fifth embodiment may employ the configuration of the third embodiment in which a transformation matrix W' is generated as an ear shape model E, the transformation matrix W' being obtained by removing (a) prescribed row(s) from the lower rows of the transformation matrix W with M rows and M columns. Furthermore, the fifth embodiment may also employ the configuration of the fourth embodiment. Specifically, from the image data $D_G$ received from the terminal device 62, an estimated three-dimensional shape $Z_A$ of the target ear is identified using the configuration and the processes of the fifth embodiment, and head-related transfer functions F corresponding to a target shape Z including the estimated three-dimensional shape $Z_A$ are distributed to the terminal device 62.

Modifications

The embodiments described above can be modified in a variety of ways. Specific modes of modification will now be described. Two or more modes selected from the following examples may be combined, as appropriate, in so far as combination of the modes is workable.

(1) As will be understood from equation (5) above, the ear shape data generator 42 calculates ear shape data $v_{(k)}$ of a candidate ear by multiplying a principal component weight vector $w_{(k)}$ by an inverse matrix $W^{-1}$ of a transformation matrix W. As such, an ear shape model E may include an inverse matrix $W^{-1}$ in place of a transformation matrix W.

Moreover, in the first to fourth embodiments, the ear shape data generator 42 calculates ear shape data $v_{(k)}$ of a candidate ear by calculation of equation (5) using a transformation matrix W and a mean vector μ, although the use of a mean vector μ may be omitted. For example, from among N ear shape data $v_{(1)}$ to $v_{(N)}$, one representative set of ear shape data $v_{(n)}$ may be used in place of a mean vector μ in equation (5). In the calculation of ear shape data v of the target ear in the fifth embodiment, the use of a mean vector μ may likewise be omitted. In other words, a mean vector μ is not an essential element of an ear shape model E. As will be understood from the above description, a statistics processor 36 is comprehensively expressed as an element that generates an ear shape model E that either includes a transformation matrix W calculated by performing principal component analysis on N ear shape data $v_{(1)}$ to $v_{(N)}$ of sample ears, or includes an inverse matrix $W^{-1}$ of the transformation matrix W.

(2) In the embodiments described above, an estimated three-dimensional shape $Z_B$ of the left ear is identified from an estimated three-dimensional shape $Z_A$ of the right ear (target ear) of the subject, and a target shape Z is generated by joining the estimated three-dimensional shapes $Z_A$ and $Z_B$ to a head shape $Z_H$. However, a method of generating a target shape Z is not limited to the above example. For example, the ear shape model generator 30 may generate an ear shape model E for each of the left and right ears, by executing an ear shape model generation process $S_A$ that is substantially the same as that in the first embodiment. A target shape Z is generated by joining to a head shape $Z_H$ an estimated three-dimensional shape $Z_A$ of the right ear identified by using the ear shape model E of the right ear, and an estimated three-dimensional shape $Z_B$ of the left ear identified by using the ear shape model of the left ear. Thus, the ear shape model generation process $S_A$ or the ear shape analysis process $S_B$ may be executed individually for each of the left and right ears. Furthermore, in the embodiments described above, a target shape Z is generated using a head shape $Z_H$ that is either a shape of a specific dummy head or an average shape of heads of a large number of unspecified human beings. However, a head shape $Z_H$ that reflects the shape of the head of each individual subject may be used instead. A method substantially the same as the ear shape model generation process $S_A$ described in the modes described above may be used to identify a head shape $Z_H$ of a subject.

(3) A configuration of an audio processor 50 is not limited to the example given in the embodiments described above. For example, a configuration shown in FIG. 21 or FIG. 22 may be employed. The audio processor 50 shown in FIG. 21 includes a sound field controller 52, a convolution calculator $54_R$, a convolution calculator $54_L$, a reverberation generator 56, and a signal adder 58. Operations of the convolution calculators $54_R$ and $54_L$ are substantially the same as those in the first embodiment. The reverberation generator 56 generates from an audio signal $X_A$ a reverberant (late reverberant) sound that occurs in a virtual acoustic space. Acoustic characteristics of the reverberant sound generated by the reverberation generator 56 are controlled by the sound field controller 52. The signal adder 58 adds the reverberant sound generated by the reverberation generator 56 to a signal having been processed by the convolution calculator $54_R$, and thereby generates an audio signal $X_{B\_R}$ for a right channel. Likewise, the signal adder 58 adds the reverberant sound generated by the reverberation generator 56 to a signal having been processed by the convolution calculator $54_L$, and thereby generates an audio signal $X_{B\_L}$ for a left channel.

Figure 22:
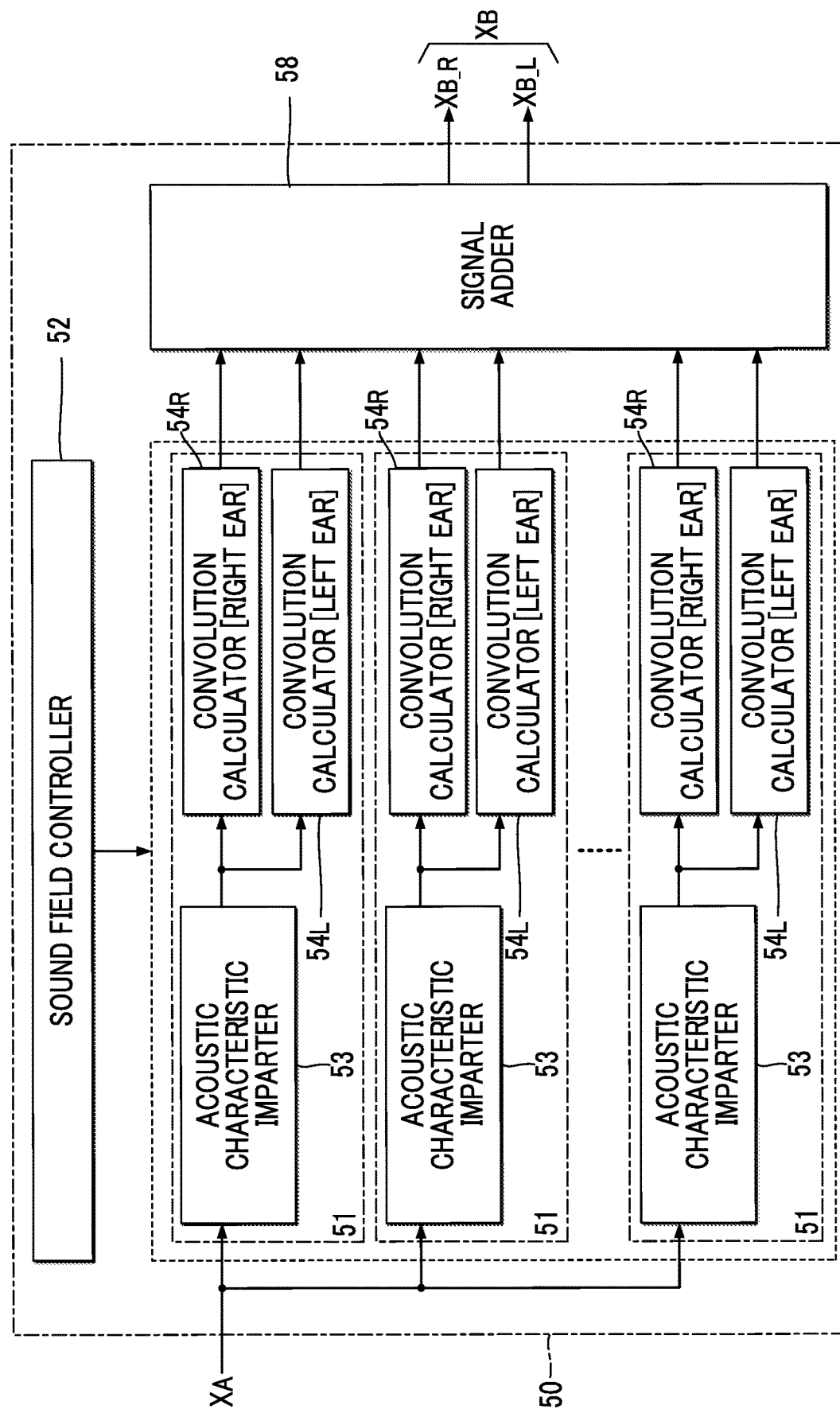
FIG. 22 is a block diagram showing a configuration of the audio processor according to a modification.

The audio processor 50 shown in FIG. 22 includes a sound field controller 52, a plurality of adjustment processors 51, and a signal adder 58. Each of the adjustment processors 51 simulates a propagation path through which a sound produced at a sound source location arrives to a listening location in a virtual acoustic space, and the propagation paths simulated differ from each other. Specifically, any one of the adjustment processors 51 includes an acoustic characteristic imparter 53, a convolution calculator $54_R$, and a convolution calculator $54_L$. The acoustic characteristic imparter 53 adjusts an amplitude or a phase of an audio signal $X_A$, and thereby simulates wall reflection in a propagation path in the acoustic space, as well as a delay and distance attenuation resulting from a distance existing in the propagation path. Characteristics imparted by each acoustic characteristic imparter 53 to an audio signal $X_A$ are controlled by the sound field controller 52 so as to be variable in accordance with a variable pertaining to the acoustic space (the size or the shape of the acoustic space, sound reflectance of a wall, a sound source location, a listening location, etc.).

The convolution calculator $54_R$ convolves into the audio signal $X_A$ a head-related transfer function F of the right ear selected by the sound field controller 52, and the convolution calculator $54_L$ convolves into the audio signal $X_A$ a head-related transfer function F of the left ear selected by the sound field controller 52. The sound field controller 52 provides to the convolution calculator $54_R$ a head-related transfer function F between a position of a mirror-image sound source and the right ear on a propagation path in the acoustic space, and provides to the convolution calculator $54_L$ a head-related transfer function F between the position of the mirror-image sound source and the left ear on a propagation path in the acoustic space. The signal adder 58 adds up signals generated by the respective adjustment processors 51 (convolution calculators $54_R$), and generates an audio signal $X_{B\_R}$ for a right channel. Likewise, the signal adder 58 adds up signals generated by the respective adjustment processors 51 (convolution calculators $54_L$), and generates an audio signal $X_{B\_L}$ for a left channel.

Figure 21:
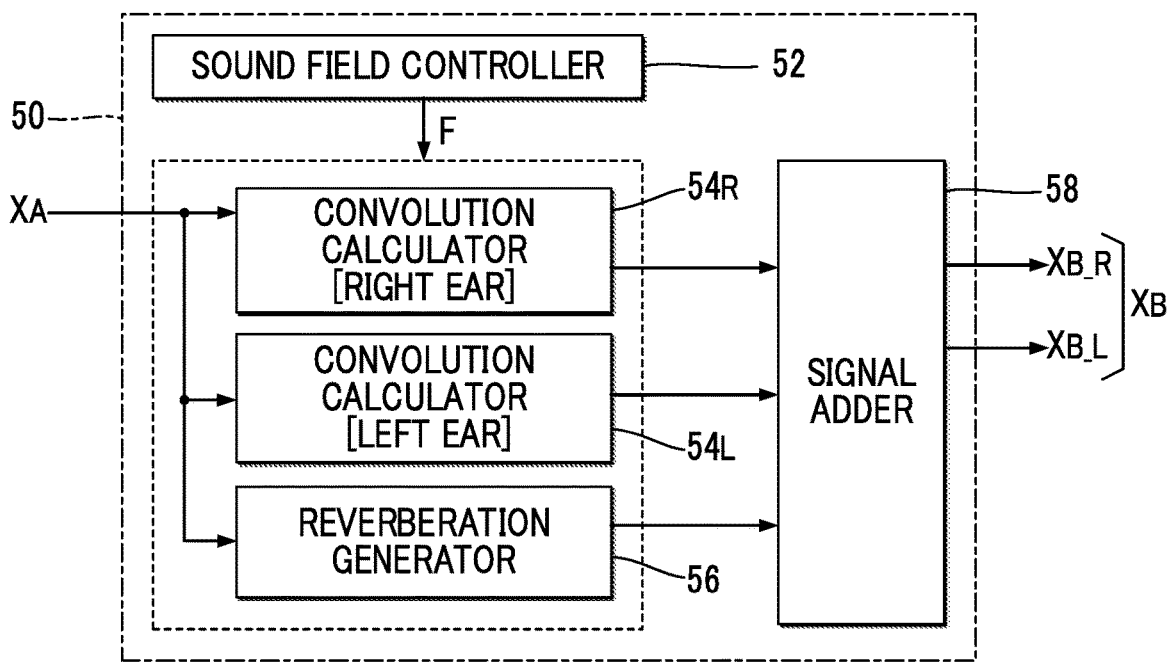
FIG. 21 is a block diagram showing a configuration of the audio processor according to a modification.

The configurations in FIGS. 21 and 22 may be combined. For example, an audio signal $X_B$ may be generated, which includes early-reflected sounds generated by the adjustment processors 51 in FIG. 22 and a reverberant sound generated by the reverberation generator 56 in FIG. 21.

(4) In the first to fourth embodiments, the image searcher 442 selects, as three-dimensional shape data $D_Z$ of the target ear, three-dimensional shape data $D_{C(k)}$ of a candidate ear that corresponds to a candidate ear image $G_{C(k)}$ having the smallest difference $\varepsilon_{(k)}$ from the target ear image $G_U$, from among K three-dimensional shape data $D_{C(1)}$ to $D_{C(K)}$ generated by the image generator 441. The image searcher 442 according to another embodiment searches for a principal component weight vector $w_{(k)}$ that corresponds to a candidate ear having the smallest difference $\varepsilon_{(k)}$ from the target ear image $G_U$, among K principal component weight vectors $w_{(1)}$ to $w_{(K)}$. In the above configuration, an estimated three-dimensional shape $Z_A$ of the target ear is identified by applying the principal component weight vector $w_{(k)}$ found by the image searcher 442 to an ear shape model E.

(5) A format of the image data $D_G$ may be freely selected. Specifically, data obtained by translating a three-dimensional shape of the target ear into a two-dimensional plane may, for example, be used for the image data $D_G$, in place of data that represents as a target ear image $G_U$ a planar image captured of the target ear (as set out in the embodiments described above). Alternatively, data indicating a parameter related to the shape of the target ear (e.g., data indicating feature points extracted from an image of the target ear) may be used as the image data $D_G$. As will be understood from the above examples, a concept of the image data $D_G$ encompasses data of a freely-selected format that enables identification of a target ear image $G_U$ that can be compared with a candidate ear image $G_{C(k)}$.

(6) In the first to third embodiments, an audio processing device 100 including an ear shape model generator 30, an ear shape analyzer 40, and an audio processor 50 is described, but the present invention may be expressed as an ear shape model generation device including an ear shape model generator 30, or as an ear shape analysis device including an ear shape analyzer 40. The same is applicable to the fifth embodiment. The ear shape model generation device may or may not include either or both an ear shape analyzer 40 and an audio processor 50, and the ear shape analysis device may or may not include either or both an ear shape model generator 30 and an audio processor 50.

(7) The ear shape model generation device or the ear shape analysis device is realized as a result of a control device 22 (such as a CPU) cooperating with a program, as is described in each of the embodiments described above. For example, the program for generating an ear shape model according to the first embodiment causes a computer to realize a sample ear analyzer 34 and a statistics processor 36, for the purpose of generating an ear shape model E used to generate a candidate ear image $G_{C(k)}$ to be compared with a target ear image $G_U$ represented by image data $D_G$. The sample ear analyzer 34 generates, for each of N sample ears, ear shape data $v_{(n)}$ indicating a difference between a point group $P_{S(n)}$ representing a three-dimensional shape of a sample ear and a point group $P_R$ representing a three-dimensional shape of a reference ear; and the statistics processor 36 calculates a transformation matrix W (a transformation matrix W' in the third embodiment) for translating ear shape data $v_{(n)}$ into a principal component weight vector $w_{(n)}$ indicating a weight of each principal component, by performing principal component analysis on N ear shape data $v_{(1)}$ to $v_{(N)}$ generated by the sample ear analyzer 34, and generates an ear shape model E including either the transformation matrix W or an inverse matrix $W^{-1}$ thereof.

Furthermore, the program for ear shape analysis according to the first embodiment causes, for example, a computer to realize an ear shape data generator 42, an image generator 441, and an image searcher 442. The ear shape data generator 42 generates, for each of K candidate ears, ear shape data $v_{(k)}$ indicating a difference between a point group $P_R$ representing a three-dimensional shape of the reference ear and a point group $P_{C(k)}$ representing a three-dimensional shape of a candidate ear, by applying each of K principal component weight vectors $w_{(1)}$ to $w_{(K)}$ (indicating weights of respective principal components) to an ear shape model E for translating a principal component weight vector $w_{(n)}$ into ear shape data $v_{(n)}$, the ear shape model E being generated by performing principal component analysis on each of ear shape data $v_{(n)}$ of sample ears (each ear shape data $v_{(n)}$ indicating a difference between the point group $P_R$ representing the three-dimensional shape of the reference ear and a point group $P_{S(n)}$ representing a three-dimensional shape of one of the N sample ears); based on the ear shape data $v_{(k)}$ and the point group $P_R$ representing the three-dimensional shape of the reference ear, the image generator 441 generates a candidate ear image $G_{C(k)}$ for each of the K candidate ears, each candidate ear image $G_{C(k)}$ representing a candidate ear; and the image searcher 442 compares each of the K candidate ear images $G_{C(1)}$ to $G_{C(K)}$ with the target ear image $G_U$ of the target ear represented by the image data $D_G$, and identifies as an estimated three-dimensional shape $Z_A$ of the target ear an ear shape that corresponds to a candidate ear corresponding to a candidate ear image $G_{C(k)}$ having the smallest difference $\varepsilon_{(k)}$ from the target ear image $G_U$.

The programs according to the different modes described above as examples may be provided by being stored on a computer-readable recording medium for installation in a computer. For instance, the storage medium may be a non-transitory storage medium, a preferable example of which is an optical storage medium, such as a CD-ROM (optical disc), and may also be a freely-selected form of well-known storage media, such as a semiconductor storage medium and a magnetic storage medium. The "non-transitory storage medium" is inclusive of any computer-readable recording media with the exception of a transitory, propagating signal, and does not exclude volatile recording media.

The programs described above may be provided by being distributed via a communication network for installation in a computer. The present invention may be expressed as an operation method of an ear shape model generation device (ear shape model generation method), or as an operation method of an ear shape analysis device (ear shape analysis method).

(8) Preferred modes of the present invention as derived from the specific embodiments illustrated above are described below.

First Mode

An ear shape analysis method according to a preferred mode (the first mode) of the present invention is implemented by a computer and the method includes: generating an ear shape data set by applying a principal component weight vector to an ear shape model, the ear shape model indicating a relation between ear shape data sets and principal component weight vectors, each ear shape data set indicating a difference between a point group representing a three-dimensional shape of an ear and a point group representing a three-dimensional shape of a reference ear, and each principal component weight vector indicating weights of principal components of the corresponding ear shape data set; and identifying from the generated ear shape data set an estimated three-dimensional shape of a target ear corresponding to a target ear image represented by image data. In the first mode, an estimated three-dimensional shape of the target ear is identified from ear shape data generated by applying a principal component weight vector to an ear shape model indicating a relation between ear shape data sets and principal component weight vectors. Accordingly, a probability of misestimating an ear shape can be reduced, compared to a configuration in which the three-dimensional shape of a target ear is estimated by deforming (morphing) a given shape.

Second Mode

In a preferred example (the second mode) of the first mode, the generated ear shape data set is one of a plurality of ear shape data sets, each corresponding to one of a plurality of candidate ears, and the generating the ear shape data set includes applying to the ear shape model each of a plurality of principal component weight vectors including the principal component weight vector, to generate each of the plurality of ear shape data sets, and the identifying the estimated three-dimensional shape includes, generating for the plurality of candidate ears a plurality of candidate ear images, each representing a corresponding candidate ear in accordance with the point group representing the three-dimensional shape of the reference ear and the ear shape data set of the candidate ear, and comparing the target ear image represented by the image data with each of the plurality of candidate ear images generated for the plurality of candidate ears, to identify as the estimated three-dimensional shape of the target ear an ear shape that corresponds to a candidate ear corresponding to a candidate ear image that has the smallest difference among differences existing between the target ear image and the respective candidate ear images, from among the plurality of candidate ear images. In the second mode, the target ear image and each of the plurality of candidate ear images generated using the ear shape model are compared with each other, and an ear shape that corresponds to a candidate ear of a candidate ear image having the smallest difference from the target ear image is identified as an estimated three-dimensional shape of the target ear. Accordingly, an advantage is obtained in that an estimated three-dimensional shape of the target ear can be identified by use of a simple image comparison process.

Third Mode

In a preferred example (the third mode) of the second mode, the generating each candidate ear image includes generating a candidate ear image of each candidate ear observed from a viewpoint conforming to conditions close to conditions used when the target ear represented by the image data was captured. In the third mode, there is generated a candidate ear image that represents a candidate ear viewed from a direction close to a direction when the target ear was captured as the target ear image. Accordingly, an advantage is obtained in that an appropriate candidate ear having a three-dimensional shape close to that of the target ear can be selected; in contrast to a case where observation conditions for a candidate ear corresponding to a candidate ear image do not match those used when the target ear image was captured.

Fourth Mode

In a preferred example (the fourth mode) of either the second or third mode, the generating the ear shape data set includes, applying each of the principal component weight vectors to the ear shape model, to generate the ear shape data set of each candidate ear, the ear shape data set including a plurality of translation vectors corresponding to respective points constituting a first group that is a part of the point group of the reference ear, and by interpolation of the plurality of translation vectors included in the ear shape data set of each candidate ear, generating translation vectors corresponding to respective points constituting a second group of the point group of the reference ear, the second group being constituted by all points of the point group of the reference ear other than the points constituting the first group, and the generating each candidate ear image includes generating each candidate ear image by moving each of the points constituting the first group of the point group of the reference ear in accordance with a corresponding one of the plurality of translation vectors of the ear shape data set of the candidate ear, and by moving each of the points constituting the second group of the point group of the reference ear in accordance with a corresponding one of the translation vectors generated by the interpolation. In the fourth mode, translation vectors corresponding to the points constituting the second group of the point group of the reference ear are generated by interpolation of a plurality of translation vectors included in ear shape data of a candidate ear, and therefore, there is no need to generate translation vectors for the entirety of the point group of the reference ear using the ear shape model. Accordingly, an advantage is obtained in that a load is reduced in a process of generating ear shape data of a candidate ear by applying a principal component weight vector to an ear shape model, or in a process of generating an ear shape model.

Fifth Mode

In a preferred example (the fifth mode) of the first mode, the ear shape analysis method further includes generating a principal component weight vector by applying the target ear image represented by the image data to a neural network indicating a relation between ear images and principal component weight vectors, and the generating the ear shape data set includes generating an ear shape data set of the target ear by applying the principal component weight vector generated by the neural network to the ear shape model, and the identifying the estimated three-dimensional shape includes identifying the estimated three-dimensional shape of the target ear in accordance with the point group representing the three-dimensional shape of the reference ear and the ear shape data set of the target ear. In the fifth mode, a principal component weight vector generated by applying the target ear image to a neural network is applied to the ear shape model, and accordingly, there is no need to repeat generation of a candidate ear image and comparison of a candidate ear image with the target ear image. Thus, an advantage is obtained in that an amount of calculation necessary for identifying an estimated three-dimensional shape of the target ear is reduced, compared to the second mode in which generation of a candidate ear image and comparison of a candidate ear image with the target ear image are repeated multiple times.

Sixth Mode

In a preferred example (the sixth mode) of any one of the first to fifth modes, the ear shape analysis method further includes calculating a head-related transfer function corresponding to the estimated three-dimensional shape. According to the first to fifth modes, a probability of misestimating an ear shape is reduced as described above, and therefore, an advantage is obtained in that it is possible to identify head-related transfer functions F, the use of which enables a listener with the target ear to perceive an appropriate location of the sound image.

Seventh Mode

In a preferred example (the seventh mode) of the sixth mode, the ear shape analysis method further includes receiving the image data from a terminal device, and transmitting to the terminal device the head-related transfer function calculated from the image data. In the seventh mode, an estimated three-dimensional shape of the target ear is identified from the image data received from the terminal device, and a head-related transfer function corresponding to the estimated three-dimensional shape is transmitted to the terminal device. Accordingly, an advantage is obtained in that there is no need to perform at a terminal device identification of an estimated three-dimensional shape of the target ear or calculation of a head-related transfer function for the estimated three-dimensional shape.

Eighth Mode

An ear shape analysis device according to a preferred mode (the eighth mode) of the present invention includes: an ear shape data generator configured to generate an ear shape data set by applying a principal component weight vector to an ear shape model, the ear shape model indicating a relation between ear shape data sets and principal component weight vectors, each ear shape data set indicating a difference between a point group representing a three-dimensional shape of an ear and a point group representing a three-dimensional shape of a reference ear, and each principal component weight vector indicating weights of principal components of the corresponding ear shape data set; and an ear shape identifier configured to identify, from the ear shape data set generated by the ear shape data generator, an estimated three-dimensional shape of a target ear corresponding to a target ear image represented by image data. In the eighth mode, an estimated three-dimensional shape of the target ear is identified from ear shape data generated by applying a principal component weight vector to an ear shape model indicating a relation between ear shape data sets and principal component weight vectors. Accordingly, a probability of misestimating an ear shape can be reduced, compared to a configuration in which the three-dimensional shape of a target ear is estimated by deforming a given shape.

Ninth Mode

In a preferred example (the ninth mode) of the eighth mode, the generated ear shape data set is one of a plurality of ear shape data sets, each corresponding to one of a plurality of candidate ears, and the ear shape data generator applies to the ear shape model each of a plurality of principal component weight vectors including the principal component weight vector, to generate each of the ear shape data sets for the plurality of candidate ears, and the ear shape identifier includes, an image generator configured to generate for the plurality of candidate ears a plurality of candidate ear images, each representing a corresponding candidate ear, in accordance with the point group representing the three-dimensional shape of the reference ear and the ear shape data set of the candidate ear, and an image searcher configured to compare the target ear image represented by the image data with each of the plurality of candidate ear images generated for the plurality of candidate ears, to identify as the estimated three-dimensional shape of the target ear an ear shape that corresponds to a candidate ear corresponding to a candidate ear image that has the smallest difference among differences existing between the target ear image and the respective candidate ear images, from among the plurality of candidate ear images. In the ninth mode, the target ear image and each of the plurality of candidate ear images generated using the ear shape model are compared with each other, and an ear shape that corresponds to a candidate ear corresponding to a candidate ear image having the smallest difference from the target ear image is identified as an estimated three-dimensional shape of the target ear. Accordingly, an advantage is obtained in that an estimated three-dimensional shape of the target ear can be identified by use of a simple image comparison process.

Tenth Mode

The ear shape analysis device according to a preferred example (the tenth mode) of the eighth mode further includes an estimation processor configured to generate a principal component weight vector by applying the target ear image represented by the image data to a neural network indicating a relation between ear images and principal component weight vectors, and the ear shape data generator generates an ear shape data set of the target ear by applying the principal component weight vector generated by the neural network to the ear shape model, and the ear shape identifier identifies the estimated three-dimensional shape of the target ear in accordance with the point group representing the three-dimensional shape of the reference ear and the ear shape data set of the target ear. In the tenth mode, a principal component weight vector generated by applying the target ear image to a neural network is applied to the ear shape model, and therefore, there is no need to repeat generation of a candidate ear image and comparison of a candidate ear image with the target ear image. Accordingly, an advantage is obtained in that an amount of calculation necessary for identifying an estimated three-dimensional shape of the target ear is reduced; in contrast to the ninth mode in which generation of a candidate ear image and comparison of a candidate ear image with the target ear image are repeated multiple times.

Eleventh Mode

A preferred example, namely, the eleventh mode of the present invention is an ear shape model generation method implemented by a computer to generate an ear shape model used in generating a candidate ear image for comparison with a target ear image represented by image data, the method including: generating, for a plurality of sample ears, a plurality of ear shape data sets, each indicating a difference between a point group representing a three-dimensional shape of a corresponding sample ear and a point group representing a three-dimensional shape of a reference ear, and calculating a transformation matrix for translating ear shape data into a principal component weight vector indicating weights of principal components, by performing principal component analysis on the plurality of generated ear shape data sets, to generate the ear shape model including the transformation matrix or an inverse matrix of the transformation matrix. In the eleventh mode, the ear shape model used in estimating the three-dimensional shape of the target ear reflects statistical tendencies of three-dimensional shapes of a plurality of sample ears. Accordingly, an advantage is obtained in that the three-dimensional shape of the target ear can be estimated with high precision.

Twelfth Mode

In a preferred example (the twelfth mode) of the eleventh mode, the generating the ear shape model includes calculating, for the plurality of sample ears, a mean vector of the ear shape data sets, and generating the ear shape model including the mean vector. In the twelfth mode, there is generated an ear shape model that includes a mean vector of a plurality of ear shape data sets in addition to the transformation matrix for translating ear shape data into a principal component weight vector, or the inverse matrix of the transformation matrix. Accordingly, an advantage is obtained in that an appropriate candidate ear image can be generated using this ear shape model.

Thirteenth Mode

In a preferred example (the thirteenth mode) of either the eleventh or twelfth mode, the generating the ear shape model includes removing prescribed rows from lower rows of the transformation matrix calculated by the principal component analysis, and generating the ear shape model indicating a transformation matrix resulting from the removing of the prescribed rows. In the thirteenth mode, a prescribed row is removed from the lower rows of the transformation matrix calculated by the principal component analysis, and accordingly an amount of data of the ear shape model can be reduced.

DESCRIPTION OF REFERENCE SIGNS

100: audio processing device
200: audio processing system
12: signal supply device
14: sound output device
16: communication network
22: control device
24: storage device
30: ear shape model generator
32: point group identifier
34: sample ear analyzer
36: statistics processor
40: ear shape analyzer
42: ear shape data generator
441: image generator
442: image searcher
48: function calculator
50: audio processor
51: adjustment processor
52: sound field controller
53: acoustic characteristic imparter
54$_R$, 54$_L$: convolution calculators
56: reverberation generator
58: signal adder
72, 74: communication devices

What is claimed is:

1. An ear shape analysis method implemented by a computer, the method comprising:

generating a first ear shape data set indicating a difference between a three-dimensional shape of an ear and a three-dimensional shape of a reference ear by applying a first principal component weight vector to an ear shape model reflecting statistical tendencies of three-dimensional shapes of ears; and identifying from the generated first ear shape data set an estimated three-dimensional shape of a target ear corresponding to a target ear image represented by image data.

2. The ear shape analysis method according to claim 1, wherein the ear shape model indicates a relation between second ear shape data sets and second principal component weight vectors, each second ear shape data set indicating a difference between a point group representing a three-dimensional shape of an ear and a point group representing a three-dimensional shape of a reference ear, and each second principal component weight vector indicating weights of principal components of the corresponding second ear shape data set.

3. The ear shape analysis method according to claim 2, wherein the generated first ear shape data set is one of a plurality of first ear shape data sets, each corresponding to one of a plurality of candidate ears, and the generating the first ear shape data set includes applying to the ear shape model each of a plurality of first principal component weight vectors including the first principal component weight vector, to generate each of the plurality of first ear shape data sets, and the identifying the estimated three-dimensional shape includes, generating for the plurality of candidate ears a plurality of candidate ear images, each representing a corresponding candidate ear in accordance with the point group representing the three-dimensional shape of the reference ear and the first ear shape data set of the candidate ear, and comparing the target ear image represented by the image data with each of the plurality of candidate ear images generated for the plurality of candidate ears, to identify as the estimated three-dimensional shape of the target ear an ear shape that corresponds to a candidate ear corresponding to a candidate ear image that has the smallest difference among differences existing between the target ear image and the respective candidate ear images, from among the plurality of candidate ear images.

4. The ear shape analysis method according to claim 3, wherein the generating each candidate ear image includes generating a candidate ear image of each candidate ear observed from a viewpoint conforming to conditions close to conditions used when the target ear represented by the image data was captured.

5. The ear shape analysis method according to claim 3, wherein the generating the first ear shape data set includes, applying each of the first principal component weight vectors to the ear shape model, to generate the first ear shape data set of each candidate ear, the first ear shape data set including a plurality of translation vectors corresponding to respective points constituting a first group that is a part of the point group of the reference ear, and by interpolation of the plurality of translation vectors included in the first ear shape data set of each candidate ear, generating translation vectors corresponding to respective points constituting a second group of the point group of the reference ear, the second group being constituted by all points of the point group of the reference ear other than the points constituting the first group, and the generating each candidate ear image includes generating each candidate ear image by moving each of the points constituting the first group of the point group of the reference ear in accordance with a corresponding one of the plurality of translation vectors of the first ear shape data set of the candidate ear, and by moving each of the points constituting the second group of the point group of the reference ear in accordance with a corresponding one of the translation vectors generated by the interpolation.

6. The ear shape analysis method according to claim 2, further comprising:

generating a principal component weight vector by applying the target ear image represented by the image data to a neural network indicating a relation between ear images and principal component weight vectors, wherein the generating the first ear shape data set includes generating a first ear shape data set of the target ear by applying the principal component weight vector generated by the neural network to the ear shape model, and the identifying the estimated three-dimensional shape includes identifying the estimated three-dimensional shape of the target ear in accordance with the point group representing the three-dimensional shape of the reference ear and the first ear shape data set of the target ear.

7. The ear shape analysis method according to claim 1, further comprising calculating a head-related transfer function corresponding to the estimated three-dimensional shape.

8. The ear shape analysis method according to claim 7, further comprising receiving the image data from a terminal device, and transmitting to the terminal device the head-related transfer function calculated from the image data.

9. An ear shape analysis device, comprising an ear shape data generator configured to generate a first ear shape data set indicating a difference between a three-dimensional shape of an ear and a three-dimensional shape of a reference ear by applying a first principal component weight vector to an ear shape model reflecting statistical tendencies of three-dimensional shapes of ears; and an ear shape identifier configured to identify, from the first ear shape data set generated by the ear shape data generator, an estimated three-dimensional shape of a target ear corresponding to a target ear image represented by image data.

10. The ear shape analysis device according to claim 9, wherein the ear shape model indicates a relation between second ear shape data sets and second principal component weight vectors, each second ear shape data set indicating a difference between a point group representing a three-dimensional shape of an ear and a point group representing a three-dimensional shape of a reference ear, and each second principal component weight vector indicating weights of principal components of the corresponding second ear shape data set.

11. The ear shape analysis device according to claim 10, wherein the generated first ear shape data set is one of a plurality of first ear shape data sets, each corresponding to one of a plurality of candidate ears, and the ear shape data generator applies to the ear shape model each of a plurality of first principal component weight vectors including the first principal component weight vector, to generate each of the first ear shape data sets for the plurality of candidate ears, and the ear shape identifier includes, an image generator configured to generate for the plurality of candidate ears a plurality of candidate ear images, each representing a corresponding candidate ear, in accordance with the point group representing the three-dimensional shape of the reference ear and the first ear shape data set of the candidate ear, and an image searcher configured to compare the target ear image represented by the image data with each of the plurality of candidate ear images generated for the plurality of candidate ears, to identify as the estimated three-dimensional shape of the target ear an ear shape that corresponds to a candidate ear corresponding to a candidate ear image that has the smallest difference among differences existing between the target ear image and the respective candidate ear images, from among the plurality of candidate ear images.

12. The ear shape analysis device according to claim 10, further comprising:

an estimation processor configured to generate a principal component weight vector by applying the target ear image represented by the image data to a neural network indicating a relation between ear images and principal component weight vectors, wherein the ear shape data generator generates a first ear shape data set of the target ear by applying the principal component weight vector generated by the neural network to the ear shape model, and the ear shape identifier identifies the estimated three-dimensional shape of the target ear in accordance with the point group representing the three-dimensional shape of the reference ear and the first ear shape data set of the target ear.

13. An ear shape model generation method implemented by a computer to generate an ear shape model used in generating a candidate ear image for comparison with a target ear image represented by image data, the method comprising:

generating, for a plurality of sample ears, a plurality of ear shape data sets, each indicating a difference between a point group representing a three-dimensional shape of a corresponding sample ear and a point group representing a three-dimensional shape of a reference ear, and calculating a transformation matrix for translating ear shape data into a principal component weight vector indicating weights of principal components, by performing principal component analysis on the plurality of generated ear shape data sets, to generate the ear shape model including the transformation matrix or an inverse matrix of the transformation matrix.

14. The ear shape model generation method according to claim 13, wherein the generating the ear shape model includes calculating, for the plurality of sample ears, a mean vector of the ear shape data sets, and generating the ear shape model including the mean vector.

15. The ear shape model generation method according to claim 13, wherein the generating the ear shape model includes removing prescribed rows from lower rows of the transformation matrix calculated by the principal component analysis, and generating the ear shape model indicating a transformation matrix resulting from the removing of the prescribed rows.

\* \* \* \* \*